US011162086B2

(12) United States Patent
Liszka et al.

(10) Patent No.: US 11,162,086 B2
(45) Date of Patent: *Nov. 2, 2021

(54) LIPASE ENZYMES

(71) Applicant: BASF SE, Ludwigshafen (DE)

(72) Inventors: Michael Liszka, San Diego, CA (US); Jochen Kutscher, Illertissen (DE); Aditi Prashar, San Diego, CA (US); Cristina Pop, San Diego, CA (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/612,515

(22) PCT Filed: May 10, 2018

(86) PCT No.: PCT/US2018/031956
§ 371 (c)(1),
(2) Date: Nov. 11, 2019

(87) PCT Pub. No.: WO2018/209018
PCT Pub. Date: Nov. 15, 2018

(65) Prior Publication Data
US 2020/0205423 A1    Jul. 2, 2020

Related U.S. Application Data

(60) Provisional application No. 62/505,500, filed on May 12, 2017.

(51) Int. Cl.
*C12N 9/20* (2006.01)
*C12N 15/01* (2006.01)
*C11D 3/386* (2006.01)
*A21D 8/04* (2006.01)
*A61K 38/00* (2006.01)

(52) U.S. Cl.
CPC .............. *C12N 9/20* (2013.01); *A21D 8/042* (2013.01); *C11D 3/38627* (2013.01); *C11D 3/38636* (2013.01); *C11D 3/38645* (2013.01); *C12Y 203/02013* (2013.01); *C12Y 301/01003* (2013.01); *C12Y 301/01004* (2013.01); *C12Y 301/0105* (2013.01); *C12Y 301/01013* (2013.01); *C12Y 301/01026* (2013.01); *C12Y 301/01072* (2013.01); *C12Y 301/01074* (2013.01); *C12Y 301/03008* (2013.01); *C12Y 301/03026* (2013.01); *C12Y 301/04003* (2013.01); *C12Y 301/04004* (2013.01); *C12Y 302/01001* (2013.01); *C12Y 302/01002* (2013.01); *C12Y 302/01004* (2013.01); *C12Y 302/0106* (2013.01); *C12Y 302/01008* (2013.01); *C12Y 302/01032* (2013.01); *C12Y 302/01133* (2013.01)

(58) Field of Classification Search
CPC .......................... C12N 9/20; C12Y 301/01003
See application file for complete search history.

(56) References Cited

U.S. PATENT DOCUMENTS

| 5,614,188 A * | 3/1997 | Urano ...................... C12R 1/07 424/93.46 |
| 5,869,438 A | 2/1999 | Svendsen et al. |
| 2002/0094367 A1* | 7/2002 | Fuglsang ............... A21D 8/042 426/549 |
| 2003/0003561 A1* | 1/2003 | Vind ....................... A21D 8/042 435/198 |
| 2009/0217463 A1 | 9/2009 | Souter et al. |
| 2014/0134707 A1* | 5/2014 | Juntunen ................ C11D 3/386 435/254.3 |
| 2018/0346893 A1* | 12/2018 | Hansen .............. C11D 3/38681 |
| 2018/0371438 A1* | 12/2018 | Saikia ............ C12Y 301/01004 |
| 2019/0053501 A1 | 2/2019 | Pop et al. |

FOREIGN PATENT DOCUMENTS

| WO | WO-93/00924 A1 | 1/1993 |
| WO | WO-94/014963 A1 | 7/1994 |
| WO | WO-02/00852 A2 | 1/2002 |
| WO | WO-03/035878 A2 | 5/2003 |
| WO | WO-03/89620 A2 | 10/2003 |
| WO | WO-2005/032496 A2 | 4/2005 |
| WO | WO-2005/086900 A2 | 9/2005 |
| WO | WO-2006/031699 A2 | 3/2006 |
| WO | WO-2008/036863 A2 | 3/2008 |
| WO | WO-2009/133177 A1 | 11/2009 |
| WO | WO-2011/046812 A1 | 4/2011 |
| WO | WO-2017/142904 A1 | 8/2017 |
| WO | WO-2018/209018 A1 | 11/2018 |

OTHER PUBLICATIONS

Coleman et al., The genome of Nectria haematococca: contribution of supernumerary chromosomes to gene expansion, PLoS Genet., 5(8):e1000618 (Aug. 2009).
Gerits, et al., "Single run HPLC separation coupled to evaporative light scattering detection unravels wheat flour endogenous lipid redistribution during bread dough making", LWT—Food Science and Technology, vol. 53, Issue 2, Oct. 2013, pp. 426-433.
International Application No. PCT/US18/31969, International Search Report and Written Opinion, dated Aug. 7, 2018.
International Application No. PCT/US2018/031956, International Search Report and Written Opinion, dated Oct. 3, 2018.

(Continued)

*Primary Examiner* — Scarlett Y Goon
*Assistant Examiner* — Samuel W Liu
(74) *Attorney, Agent, or Firm* — Marshall, Gerstein & Borun LLP

(57) ABSTRACT

Lipase enzymes, methods of making lipase enzymes, methods of using lipase enzymes in food, feed, personal care, detergents, grain processing, pulp and paper processing, biofuels, ethanol production, textiles, dairy processing, cocoa butter processing, cocoa extraction, dietary supplements, coffee processing, coatings, water treatment, and oil processing.

12 Claims, 2 Drawing Sheets
Specification includes a Sequence Listing.

(56) References Cited

OTHER PUBLICATIONS

NCBI Reference Sequence: XP_003050606.1, hypothetical protein NECHADRAFT_49364 [[Nectria] haematococca mpVI 77-13-4], (Aug. 28, 2009).
Needleman, et al., "A general method applicable to the search for similarities in the amino acid sequence of two proteins", Journal of Molecular Biology, vol. 48, Issue 3, Mar. 28, 1970, pp. 443-453.
Schaffarczyk et al., Lipases in wheat breadmaking: analysis and functional effects of lipid reaction products, J. Agric. Food Chem., 62(32):8229-37 (Aug. 2014).
European Search Report for EP Patent Application No. 18797619.6, dated Jan. 29, 2021, 3 pages.
Liu et al., "A novel low-temperature resistant alkaline lipase from a soda lake fungus strain Fusarium solani N4-2 for detergent formulation", Biochemical Engineering Journal, vol. 46, Issue 3, Nov. 1, 2009, pp. 265-270.
"RecName: Full=Lipase_3 domain-containing protein {ECO:0000259|Pfam:PF01764}", Database UniProt [Online], retrieved from EBI Database accession No. C7YUZ1, XP002801892, Oct. 13, 2009, 1 page.
European Search Report for EP Patent Application No. 18798843.1, dated Feb. 11, 2021, 4 pages.
Moayedallaie, et al., "Bread improvers: Comparison of a range of lipases with a traditional emulsifier", Food Chemistry, vol. 122, Issue 3, Oct. 1, 2010, pp. 495-499.

\* cited by examiner

| Lipase Variants | Fermentation | \multicolumn{19}{c|}{mg pure lipase/kg flour} | \multicolumn{4}{c|}{Controls at optimal dosage} |
|---|---|---|---|---|---|---|---|---|---|---|---|---|---|---|---|---|---|---|---|---|---|---|---|---|
| | | 0.02 | 0.04 | 0.07 | 0.09 | 0.1 | 0.14 | 0.17 | 0.24 | 0.26 | 0.29 | 0.34 | 0.39 | 0.51 | 0.58 | 0.68 | 1.02 | 1.36 | 2.04 | 2.72 | PG2.2 | LIP62 | DATEM | stdev |
| LIP101 | Normal | - | - | - | - | - | - | - | - | - | - | - | - | - | - | - | - | - | - | 12.5 | 8.8 | 8.1 | 11.0 | 1.1 |
| | Extended | - | - | - | - | - | - | - | - | - | - | - | - | - | - | - | - | - | - | 14.5 | 10.3 | 12.6 | 13.3 | 0.9 |
| LIP102 | Normal | - | - | - | - | - | - | - | - | - | - | - | - | - | - | 13.0 | 9.0 | 8.5 | 13.0 | - | 8.8 | 8.1 | 11.0 | 1.1 |
| | Extended | - | - | - | - | - | - | - | - | - | - | - | - | - | - | 10.0 | 13.0 | 13.5 | 14.0 | - | 10.3 | 12.6 | 13.3 | 0.9 |
| LIP108 | Normal | - | - | - | - | - | - | 7.5 | - | 8.0 | 12.0 | 9.0 | 11.0 | 10.5 | 9.0 | 7.0 | 9.0 | 7.0 | - | - | 8.8 | 8.1 | 11.0 | 1.1 |
| | Extended | - | - | - | - | - | - | 11.5 | - | 12.0 | 15.0 | 11.0 | 12.5 | 10.0 | 11.5 | 9.0 | 8.0 | 9.0 | - | - | 10.3 | 12.6 | 13.3 | 0.9 |
| LIP110 | Normal | - | - | - | - | - | - | 8.0 | - | 12.0 | 11.0 | 7.5 | 10.0 | 11.5 | 12.0 | 8.0 | 7.0 | 8.0 | - | - | 8.8 | 8.1 | 11.0 | 1.1 |
| | Extended | - | - | - | - | - | - | 10.0 | - | 12.0 | 13.0 | 10.5 | 12.7 | 12.0 | 12.5 | 10.0 | 10.0 | 10.0 | - | - | 10.3 | 12.6 | 13.3 | 0.9 |
| LIP117 | Normal | 2.0 | 4.5 | 3.0 | 7.7 | 8.7 | - | 4.0 | - | - | - | 3.0 | - | 2.0 | - | - | 3.0 | - | - | - | 8.8 | 8.1 | 11.0 | 1.1 |
| | Extended | 5.0 | 8.5 | 9.0 | 13.3 | 14.0 | - | 6.0 | - | - | - | 5.0 | - | 6.0 | - | - | 6.0 | - | - | - | 10.3 | 12.6 | 13.3 | 0.9 |
| LIP120 | Normal | - | 3.0 | - | 6.0 | - | - | 11.0 | - | 9.0 | - | 10.3 | 10.5 | - | 8.0 | 7.0 | 8.0 | - | 9.0 | - | 8.8 | 8.1 | 11.0 | 1.1 |
| | Extended | - | 5.0 | - | 10.0 | - | - | 13.0 | - | 12.0 | - | 14.0 | 16.0 | - | 13.5 | 13.0 | 14.0 | - | 13.0 | - | 10.3 | 12.6 | 13.3 | 0.9 |
| LIP152 | Normal | - | - | - | - | - | - | 4.0 | - | - | - | 5.0 | - | 5.0 | - | 12.0 | 10.0 | 11.0 | 12.0 | - | 8.8 | 8.1 | 11.0 | 1.1 |
| | Extended | - | - | - | 2.0 | - | - | 8.0 | - | - | - | 9.0 | - | 10.0 | - | 11.5 | 12.0 | 13.0 | 15.0 | - | 10.3 | 12.6 | 13.3 | 0.9 |
| LIP151 | Normal | - | - | - | - | - | - | 1.0 | - | - | - | 7.0 | - | 7.0 | - | 7.0 | 9.0 | 9.0 | 11.0 | - | 8.8 | 8.1 | 11.0 | 1.1 |
| | Extended | - | - | - | - | - | - | - | - | - | - | 11.0 | - | 9.0 | - | 10.0 | 9.5 | 13.0 | 14.0 | - | 10.3 | 12.6 | 13.3 | 0.9 |
| LIP156 | Normal | 1.0 | 3.0 | 10.0 | - | 7.0 | - | 12.0 | 11.5 | - | 12.0 | - | - | - | - | - | - | - | - | - | 8.8 | 8.1 | 11.0 | 1.1 |
| | Extended | 2.0 | 8.0 | 11.0 | - | 4.0 | - | 9.0 | 11.5 | - | 10.0 | - | - | - | - | - | - | - | - | - | 10.3 | 12.6 | 13.3 | 0.9 |
| LIP167 | Normal | - | (1.0) | - | (1.0) | - | - | 8.0 | 8.3 | - | - | 7.0 | - | 8.0 | - | 7.0 | - | - | - | - | 8.8 | 8.1 | 11.0 | 1.1 |
| | Extended | - | 2.0 | - | 8.0 | - | - | 12.0 | 11.3 | - | - | 12.5 | - | 11.0 | - | 10.0 | - | - | - | - | 10.3 | 12.6 | 13.3 | 0.9 |
| LIP168 | Normal | - | - | - | (1.0) | - | - | - | 2.0 | - | - | 10.0 | - | 11.0 | - | 11.0 | 11.0 | 10.0 | - | - | 8.8 | 8.1 | 11.0 | 1.1 |
| | Extended | - | - | - | (3.0) | - | - | 2.0 | 7.0 | - | - | 10.0 | - | 13.0 | - | 12.0 | 15.0 | 13.0 | - | - | 10.3 | 12.6 | 13.3 | 0.9 |
| LIP170 | Normal | - | - | - | 4.0 | - | - | 9.0 | - | - | - | 9.0 | - | 12.0 | - | 7.0 | 8.0 | - | - | - | 8.8 | 8.1 | 11.0 | 1.1 |
| | Extended | - | - | - | 1.0 | - | - | 12.0 | - | - | - | 12.0 | - | 12.0 | - | 14.0 | 15.0 | - | - | - | 10.3 | 12.6 | 13.3 | 0.9 |
| LIP171 | Normal | - | - | - | (1.0) | - | - | (3.0) | 3.0 | - | - | 7.0 | - | - | - | 9.0 | - | - | - | - | 8.8 | 8.1 | 11.0 | 1.1 |
| | Extended | - | (1.0) | - | 1.0 | - | - | 3.0 | 7.0 | - | - | 14.0 | - | - | - | 15.0 | - | - | - | - | 10.3 | 12.6 | 13.3 | 0.9 |
| LIP173 | Normal | - | - | - | - | 3.0 | - | - | 11.0 | - | - | 10.0 | - | 13.0 | - | 12.0 | - | - | - | - | 8.8 | 8.1 | 11.0 | 1.1 |
| | Extended | - | - | 1.0 | - | 12.0 | - | - | 14.0 | - | - | 13.0 | - | 11.0 | - | 17.0 | - | - | - | - | 10.3 | 12.6 | 13.3 | 0.9 |
| LIP174 | Normal | - | - | (1.0) | - | (2.0) | - | - | 2.0 | - | - | 7.0 | - | 11.0 | - | 12.0 | - | - | - | - | 8.8 | 8.1 | 11.0 | 1.1 |
| | Extended | - | - | 1.0 | - | 5.0 | - | - | 10.0 | - | - | 12.0 | - | 17.0 | - | 15.0 | - | - | - | - | 10.3 | 12.6 | 13.3 | 0.9 |

FIG. 1A

| Lipase Variants | Fermentation | mg pure lipase/kg flour | | | | | | | | | | | | | | | | | | | Controls at optimal dosage | | | |
|---|---|---|---|---|---|---|---|---|---|---|---|---|---|---|---|---|---|---|---|---|---|---|---|---|
| | | 0.02 | 0.04 | 0.07 | 0.09 | 0.1 | 0.14 | 0.17 | 0.24 | 0.26 | 0.29 | 0.34 | 0.39 | 0.51 | 0.58 | 0.68 | 1.02 | 1.36 | 2.04 | 2.72 | PG2.2 | LIP62 | DATEM | stdev |
| LIP175 | Normal | - | - | - | 3.0 | - | - | 9.0 | - | - | - | 8.0 | - | 12.0 | - | 8.0 | 7.0 | - | - | - | 8.8 | 8.1 | 11.0 | 1.1 |
| | Extended | - | - | - | 6.0 | - | - | 13.0 | - | - | - | 13.0 | - | 13.0 | - | 9.0 | 12.0 | - | - | - | 10.3 | 12.6 | 13.3 | 0.9 |
| LIP176 | Normal | - | - | 4.0 | - | - | 11.0 | - | 12.0 | - | - | 11.0 | - | 8.0 | - | 7.0 | - | - | - | - | 8.8 | 8.1 | 11.0 | 1.1 |
| | Extended | - | - | 8.0 | - | - | 12.0 | - | 13.0 | - | - | 14.0 | - | 13.0 | - | 13.0 | - | - | - | - | 10.3 | 12.6 | 13.3 | 0.9 |
| LIP180 | Normal | - | - | - | - | - | - | - | 1.0 | - | - | 7.0 | - | 9.0 | - | 7.0 | 9.0 | 8.0 | - | - | 8.8 | 8.1 | 11.0 | 1.1 |
| | Extended | - | - | - | - | - | - | - | 3.0 | - | - | 12.0 | - | 14.0 | - | 9.0 | 14.0 | 14.0 | - | - | 10.3 | 12.6 | 13.3 | 0.9 |
| LIP181 | Normal | - | - | - | - | - | 1.0 | - | 7.0 | - | - | 9.0 | - | 9.0 | - | 9.0 | 10.0 | - | - | - | 8.8 | 8.1 | 11.0 | 1.1 |
| | Extended | - | - | - | - | - | 3.0 | - | 12.0 | - | - | 14.0 | - | 15.0 | - | 14.0 | 16.0 | - | - | - | 10.3 | 12.6 | 13.3 | 0.9 |
| LIP148 | Normal | - | - | - | 9.0 | - | - | 6.0 | 8.0 | - | - | 6.5 | - | - | - | 10.0 | - | - | - | - | 8.8 | 8.1 | 11.0 | 1.1 |
| | Extended | - | - | - | 11.0 | - | - | 13.0 | 13.0 | - | - | 13.5 | - | - | - | 13.0 | - | - | - | - | 10.3 | 12.6 | 13.3 | 0.9 |
| LIP154 | Normal | - | - | - | - | - | - | 8.0 | 7.0 | - | - | 6.0 | - | 10.0 | - | - | - | - | - | - | 8.8 | 8.1 | 11.0 | 1.1 |
| | Extended | - | - | - | - | - | - | 13.0 | 16.0 | - | - | 15.0 | - | 17.0 | - | - | - | - | - | - | 10.3 | 12.6 | 13.3 | 0.9 |
| LIP157 | Normal | - | - | - | 6.0 | - | - | 10.0 | 8.5 | - | - | 8.3 | - | 9.5 | - | - | - | - | - | - | 8.8 | 8.1 | 11.0 | 1.1 |
| | Extended | - | - | - | 14.0 | - | - | 15.0 | 14.5 | - | - | 13.3 | - | 14.0 | - | - | - | - | - | - | 10.3 | 12.6 | 13.3 | 0.9 |
| LIP147 | Normal | - | 1.0 | - | 10.0 | - | - | 8.0 | - | - | - | 9.0 | - | 2.0 | - | 6.0 | - | - | - | - | 8.8 | 8.1 | 11.0 | 1.1 |
| | Extended | - | 4.0 | - | 11.0 | - | - | 12.0 | - | - | - | 10.0 | - | 7.0 | - | 11.0 | - | - | - | - | 10.3 | 12.6 | 13.3 | 0.9 |
| LIP158 | Normal | - | - | - | (1.0) | - | - | - | - | - | - | 4.0 | - | - | - | 11.0 | 11.0 | 12.0 | - | - | 8.8 | 8.1 | 11.0 | 1.1 |
| | Extended | - | - | - | (2.0) | - | - | 3.0 | - | - | - | 6.0 | - | - | - | 12.0 | 13.0 | 17.0 | - | - | 10.3 | 12.6 | 13.3 | 0.9 |
| LIP159 | Normal | - | - | - | (3.0) | - | - | 2.0 | 5.0 | - | - | - | - | 9.0 | - | - | - | - | - | - | 8.8 | 8.1 | 11.0 | 1.1 |
| | Extended | - | - | - | 2.0 | - | - | 11.0 | 13.0 | - | - | - | - | 15.0 | - | - | - | - | - | - | 10.3 | 12.6 | 13.3 | 0.9 |
| LIP160 | Normal | - | - | - | - | - | - | 10.0 | 11.0 | - | - | 11.0 | - | - | - | 11.0 | 12.0 | - | - | - | 8.8 | 8.1 | 11.0 | 1.1 |
| | Extended | - | - | - | - | - | - | 7.0 | 13.0 | - | - | 13.0 | - | - | - | 14.5 | 16.0 | - | - | - | 10.3 | 12.6 | 13.3 | 0.9 |
| LIP161 | Normal | - | - | - | - | - | - | 2.0 | 3.0 | - | - | 5.0 | - | 9.0 | - | 9.0 | 5.0 | - | - | - | 8.8 | 8.1 | 11.0 | 1.1 |
| | Extended | - | - | - | - | - | - | 7.0 | 11.0 | - | - | 13.0 | - | 12.0 | - | 15.0 | 14.0 | - | - | - | 10.3 | 12.6 | 13.3 | 0.9 |
| LIP162 | Normal | - | - | - | - | - | - | 1.0 | 7.0 | - | - | 10.0 | - | 5.0 | - | 10.0 | 8.0 | - | - | - | 8.8 | 8.1 | 11.0 | 1.1 |
| | Extended | - | - | - | - | - | - | 4.0 | 15.0 | - | - | 14.0 | - | 12.0 | - | 15.0 | 14.0 | - | - | - | 10.3 | 12.6 | 13.3 | 0.9 |

FIG. 1B

LIPASE ENZYMES

This application is a National Stage application of International Application No. PCT/US2018/031956, filed May 10, 2018, which claims priority to U.S. Provisional Patent Application No. 62/505,500, filed on May 12, 2017.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "160782_Seqlisting.txt", which was created on Oct. 31, 2019 and is 4,334 bytes in size. The subject matter of the Sequence Listing is incorporated herein in its entirety by reference.

TECHNICAL FIELD

Bread has been a staple of human nutrition for thousands of years. Bread is usually made by combining a flour, water, salt, yeast, and/or other food additives to make a dough or paste; then the dough is baked to make bread. Enzymes are known to be useful in baking because of the enzymes effects on the baking process can be similar or better than chemical alternatives, enzymes can be useful for antistaling, and increasing bread volume. Several different enzymes can be used for making bread, for example lipases have been known to improve the stability and volume of the bread; however, the industry still needs a lipase that improves volume, stability, tolerance, reduces or eliminates the additive diacetyl tartaric acid esters of monoglycerides (DATEM). This disclosure is directed to variant lipase enzymes that meets or exceeds these industrial requirements.

BRIEF SUMMARY OF THE INVENTION

A variant polypeptide comprising an amino acid sequence that is at least 80% identical to the amino acid sequence of SEQ ID NO:1, and the variant polypeptide has lipase activity.

A variant polypeptide comprising an amino acid residue insertion, deletion, or substitution to the amino acid sequence of SEQ ID NO:1, and the variant polypeptide has lipase activity.

A variant polypeptide comprising an amino acid residue insertion, deletion, or substitution is at the amino acid residue position number 23, 33, 82, 83, 84, 85, 160, 199, 254, 255, 256, 258, 263, 264, 265, 268, 308, 311, or any combination thereof to the amino acid sequence of SEQ ID NO:1, and the variant polypeptide has lipase activity.

A variant polypeptide comprising an amino acid substitution is selected from the group consisting of: Y23A, K33N, S82T, S83D, S83H, S83I, S83N, S83R, S83T, S83Y, S84S, S84N, 84'Y, 84'L, 84'S, I85A, I85C, I85F, I85H, I85L, I85M, I85P, I85S, I85T, I85V, I85Y, K160N, P199I, P199V, I254A, I254C, I254E, I254F, I254G, I254L, I254M, I254N, I254R, I254S, I2454V, I254W, I254Y, I255A, I255L, A256D, L258A, L258D; L258E, L258G, L258H, L258N, L258Q, L258R, L258S, L258T, L258V, D263G, D263K, D263P, D263R, D263S; T264A, T264D, T264G, T264I, T264L, T264N, T264S, D265A, D265G, D265K, D265L, D265N, D265S, D265T, T268A, T268G, T268K, T268L, T268N, T268S, D308A, and Y311E, or any combination thereof to the amino acid sequence of SEQ ID NO:1, and the variant polypeptide has lipase activity.

A variant polypeptide comprising an amino acid sequence that is at least 80% identical to the amino acid sequence as set forth in SEQ ID NO:1, wherein the variant polypeptide has at least one single amino acid substitution to the amino acid sequence of SEQ ID NO:1, and the one single amino acid substitution is selected from the group consisting of: Y23A, K33N, S82T, S83D, S83H, S83I, S83N, S83R, S83T, S83Y, S84S, S84N, 84'Y, 84'L, 84'S, I85A, I85C, I85F, I85H, I85L, I85M, I85P, I85S, I85T, I85V, I85Y, K160N, P199I, P199V, I254A, I254C, I254E, I254F, I254G, I254L, I254M, I254N, I254R, I254S, I2454V, I254W, I254Y, I255A, I255L, A256D, L258A, L258D; L258E, L258G, L258H, L258N, L258Q, L258R, L258S, L258T, L258V, D263G, D263K, D263P, D263R, D263S; T264A, T264D, T264G, T264I, T264L, T264N, T264S, D265A, D265G, D265K, D265L, D265N, D265S, D265T, T268A, T268G, T268K, T268L, T268N, T268S, D308A, and Y311E, to the amino acid sequence of SEQ ID NO:1; wherein the variant polypeptide has lipase activity.

A variant polypeptide comprising an amino acid sequence that is at least 80% identical to the amino acid sequence as set forth in SEQ ID NO:1, wherein the variant polypeptide has a modification as set forth in Table: 1, and the variant polypeptide has lipase activity.

A variant polypeptide wherein the variant polypeptide is encoded by a nucleic acid sequence that is at least 80% identical the nucleic acid sequence as set forth in SEQ ID NO:2, and the variant polypeptide has lipase activity.

A variant nucleotide of the nucleic acid sequence as set forth in SEQ ID NO:2, wherein the variant nucleotide is a nucleic acid sequence that is at least 80% identical to the nucleic acid sequence as set forth in SEQ ID NO:2, wherein the variant nucleotide encodes a polypeptide having lipase activity.

A variant polypeptide comprising a fragment of the full length amino acid sequence of SEQ ID NO:1, and the fragment is the variant polypeptide having lipase activity.

A variant polypeptide comprising a hybrid of at least one variant polypeptide disclosed herein, and a second polypeptide having lipase activity, wherein the hybrid has lipase activity.

A composition comprising the variant polypeptide as disclosed herein.

A composition comprising the variant polypeptide as disclosed herein, and at least a second enzyme. The composition, further comprising the second enzyme is selected from the group consisting of: a second lipase, an amylase, a xylanase, a protease, a cellulase, a glucoamylase, an Oxidoreductases, a Phospholipase and a cyclodextrin glucanotransferase.

The composition comprising the variant polypeptide as disclosed herein and further comprising a carrier, a stabilizer, a buffer, a preservative, or any combination thereof. The composition comprising the variant polypeptide as disclosed herein, wherein the carrier is a wheat flour. The composition comprising the variant polypeptide as disclosed herein, wherein the stabilizer is calcium acetate, calcium chloride, magnesium chloride, sodium chloride, sodium sulfate, guar gum, or any combination thereof. The composition comprising the variant polypeptide as disclosed herein wherein the buffer is calcium acetate, sodium acetate, sodium citrate, sodium phosphate, potassium phosphate, or any combination thereof. The composition comprising the variant polypeptide as disclosed herein wherein the preservatives are calcium acetate, sodium acetate, sodium propionate, calcium propionate, propionic acid, potassium sorbate, sorbic acid, sodium benzoate, benzoic acid, acetic acid, or any combination thereof. The composition comprising the variant polypeptide as disclosed herein wherein composition. The composition comprising the variant polypeptide as disclosed herein and one or more components selected from the group consisting of sugars like sucrose, trehalose, lactose; milk powder, gluten, granulated fat, an amino acid, a salt, an oxidant such as ascorbic acid, bromate and azodicabonamide, a reducing agent such as L-cysteine, an emulsifier such as mono-glycerides, di-glycerides, clycerol monstearate, sodium stearoyl lactylate, calcium stearoyl lactylate, polyglycerol esters of fatty acids and diacetyl tartaric acid esters of mono- and diglycerides, gums such as guar gum and xanthangum, flavors, acids such as citric acid and propionic acid, starch, modified starch, humectants such as glycerol, and preservatives.

A method of making a variant polypeptide comprising: providing a template nucleic acid sequence of SEQ ID NO:2, or disclosed herein, transforming the template nucleic acid sequence into an expression host, cultivating the expression host to produce the variant polypeptide, and purifying the variant polypeptide. The method further comprising an expression host is selected from the group consisting of: a bacterial expression system, a yeast expression system, a fungal expression system, and a synthetic expression system. The method wherein the bacterial expression system is selected from an *E. coli*, a *Bacillus*, a *Pseudomonas*, and a *Streptomyces*. The method wherein the yeast expression system is selected from a *Candida*, a *Pichia*, a *Saccharomyces*, a *Schizosaccharomyces*. The method wherein the fungal expression system is selected from a *Penicillium*, an *Aspergillus*, a *Fusarium*, a *Myceliopthora*, a *Rhizomucor*, a *Rhizopus*, a *Thermomyces*, and a *Trichoderma*.

A method of preparing a dough or a baked product prepared from the dough, without the addition of an emulsifier, the method comprising adding one of the variant polypeptides as disclosed herein to the dough and baking it. The method wherein the emulsifier is selected from the group consisting of: calcium stearoyl lactylate (CSL), diacetyl tartaric acid esters of monoglycerides (DATEM), ethoxylated mono- and diglycerides (EMG), polysorbates (PS), sodium stearoyl lactylate (SSL), and succinylated monoglycerides (SMG).

A pre-mix for dough or a baked product prepared from a dough, comprising at least one of the variant polypeptides as disclosed herein.

BRIEF DESCRIPTION OF THE SEVERAL VIEWS OF THE DRAWING

FIG. 1A and FIG. 1B, shows results for baking trials.

DETAILED DESCRIPTION OF THE INVENTION

Bread includes, but is not limited to: rolls, buns, pastries, cakes, flatbreads, pizza bread, pita bread, wafers, pie crusts naan, lavish, pitta, focaccia, sourdoughs, noodles, cookies, tortillas, pancakes, crepes, croutons, and biscuits. Baking bread generally involves mixing ingredients to form dough, kneading, rising, shaping, baking, cooling and storage. The ingredients used for making dough generally include flour, water, salt, yeast, and other food additives.

Flour is generally made from wheat and can be milled for different purposes such as making bread, pastries, cakes, biscuits pasta, and noodles. Alternatives to wheat flour include, but are not limited to: almond flour, coconut flour, chia flour, corn flour, barley flour, spelt flour, soya flour, hemp flour, potato flour, quinoa, teff flour, rye flour, amaranth flour, arrowroot flour, chick pea (garbanzo) flour, cashew flour, flax meal, macadamia flour, millet flour, sorghum flour, rice flour, tapioca flour, and any combination thereof. Flour type is known to vary between different regions and different countries around the world.

Yeast breaks down sugars into carbon dioxide and water. A variety of Baker's yeast, which are usually derived from *Saccharomyces cerevisiae*, are known to those skilled in the art including, but not limited to: cream yeast, compressed yeast, cake yeast, active dry yeast, instant yeast, osmotolerant yeasts, rapid-rise yeast, deactivated yeast. Other kinds of yeast include nutritional yeast, brewer's yeast, distiller's and wine yeast.

Sweeteners include but are not limited to: liquid sugar, syrups, white (granulated) sugars, brown (raw) sugars, honey, fructose, dextrose, glucose, high fructose corn syrup, molasses, and artificial sweeteners Emulsifiers include but are not limited to diacetyl tartaric acid esters of monoglycerides (DATEM), sodium stearoyl lactylate (SSL), calcium stearoyl lactylate (CSL), ethoxylated mono- and diglycerides (EMG), polysorbates (PS), and succinylated monoglycerides (SMG).

Other food additives that can be used with the methods of this disclosure include: Lipids, oils, butter, margarine, shortening, butterfat, glycerol, eggs, diary, non-diary alternatives, thickeners, preservatives, colorants, and enzymes.

The ingredients or additives for baking can be added individually to during the baking process. The ingredients or additives can also be combined with more than one ingredient or additive to form pre-mixes and then the pre-mixes are added during the baking process. In addition, enzymes can be added directly to the flour prior to the baking process.

An enzyme is a biological molecule comprising a sequence of amino acids, wherein the enzyme can catalyze a reaction. Enzyme names are known to those skilled in the art based on the recommendations of the Nomenclature Committee of the International Union of Biochemistry and Molecular Biology (IUBMB). Enzyme names include: an EC (Enzyme Commission) number, recommended name, alternative names (if any), catalytic activity, and other factors. Enzymes are also known as a polypeptide, a protein, a peptide, an amino acid sequence, or is identified by a SEQ ID NO. In this disclosure, the alternative names for enzyme can be used interchangeably.

Different classes of enzymes are known to be useful in baking, including: Lipases E.C. 3.1.3; Alpha-amylase (E.C. 3.2.1.1); beta-amylase (E.C. 3.2.1.2); Glucan 1, 4-alpha-maltotetraohydrolase (E.C. 3.2.1.60), also known as exo-maltotetraohydrolase, G4-amylase; Glucan 1,4-alpha-maltohydrolase (E.C. 3.2.1.133), also known as maltogenic alpha-amylase; Endo-1,4-beta-xylanase (E.C. 3.2.1.8); Oxidoreductases; Phospholipase A1 (E.C. 3.1.1.32) Phospholipase A2 (E.C. 3.1.1.4); Phospholipase C (E.C. 3.1.4.3); Phospholipase D (E.C. 3.1.4.4); Galactolipase (E.C. 3.1.1.26), Cellulase (EC 3.2.1.4), Transglutaminases (EC 2.3.2.13), Phytase (EC 3.1.3.8; 3.1.3.26; and 3.1.1.72) and Protease. Enzymes are used as food ingredients, food additives, and/processing aids.

Lipases (E.C. 3.1.1.3) are hydrolytic enzymes that are known to cleave ester bonds in lipids. Lipases include phospholipases, triacylglycerol lipases, and galactolipases. Lipases have been identified from plants; mammals; and microorganisms including but not limited to: *Pseudomonas*,

*Vibrio, Acinetobacter, Burkholderia, Chromobacterium,* Cutinase from *Fusarium solani* (FSC), *Candida antarctica* A (CalA), *Rhizopus oryzae* (ROL), *Thermomyces lanuginosus* (TLL), *Rhizomucor miehei* (RML), *Aspergillus Niger, Fusarium heterosporum, Fusarium oxysporum, Fusarium culmorum* lipases.

In addition, many lipases, phospholipases, and galactolipases have been disclosed in patents and published patent applications including, but not limited to: WO1993/000924, WO2003/035878, WO2003/089620, WO2005/032496, WO2005/086900, WO2006/031699, WO2008/036863, and WO2011/046812.

Commercial lipases used in food processing and baking including, but not limited to: LIPOPAN™, NOOPAZYME, LIPOPAN MAX, LIPOPAN Xtra (available from Novozymes); PANAMORE, CAKEZYME, and BAKEZYME (available from DSM); and GRINDAMYL EXEL 16, GRINDAMYL POWERBAKE, and TS-E 861 (available from Dupont/Danisco).

A "parent" sequence (of a parent protein or enzyme, also called "parent enzyme") is the starting sequence for introduction of changes (e.g. by introducing one or more amino acid substitutions, insertions, deletions, or a combination thereof) to the sequence, resulting in "variants" of the parent sequences. The term parent enzyme (or parent sequence) includes
1. wild-type enzymes (sequences) and
2. Synthetically generated sequences (enzymes) which are used as starting sequences for introduction of (further) changes. "Enzyme variants" or "sequence variants" or "variant enzymes" refers to an enzyme that differs from its parent enzyme in its amino acid sequence to a certain extent. If not indicated otherwise, variant enzyme "having enzymatic activity" means that this variant enzyme has the same type of enzymatic activity as the respective parent enzyme.

In an embodiment, the variant polypeptide having an amino acid substitution can be a conservative amino acid substitution. A "conservative amino acid substitution" means replacement of one amino acid residue in an amino acid sequence with a different amino acid residue having a similar property at the same position compared to the parent amino acid sequence. Some examples of a conservative amino acid substitution include but are not limited to replacing a positively charged amino acid residue with a different positively charged amino acid residue; replacing a polar amino acid residue with a different polar amino acid residue; replacing a non-polar amino acid residue with a different non-polar amino acid residue, replacing a basic amino acid residue with a different basic amino acid residue, or replacing an aromatic amino acid residue with a different aromatic amino acid residue.

WIPO Standard ST.25 (1998) provides that the amino acid residues should be represented in the sequence listing using the following three-letter symbols with the first letter as a capital. The table below provides an overview of the amino acid identifiers as well as the corresponding DNA codons that encode the amino acid using the standard genetic standard. The DNA codons that encode amino acid residues can be different depending organism that is used and slightly different tables for translation of the genetic code may apply. A compilation of such non-standard code translation tables is maintained at the NCBI. For reference see e.g. www.ncbi.nlm.nih.gov/Taxonomy/Utils/wprintgc.cgi.

| Amino Acids | | | |
|---|---|---|---|
| Name | 3 letter code | 1 letter code | DNA codons |
| Alanine | Ala | A | GCA, GCC, GCG, GCT |
| Arginine | Arg | R | AGA, AGG, CGA, CGC, CGG, CGT |
| Asparagine | Asn | N | AAC, AAT |
| Aspartic acid; (Aspartate) | Asp | D | GAC, GAT |
| Cysteine | Cys | C | TGC, TGT |
| Glutamic acid; (Glutamate) | Glu | E | GAA, GAG |
| Glutamine | Gln | Q | CAA, CAG |
| Glycine | Gly | G | GGA, GGC, GGG, GGT |
| Histidine | His | H | CAC, CAT |
| Isoleucine | Ile | I | ATA, ATC, ATT |
| Leucine | Leu | L | CTA, CTC, CTG, CTT, TTA, TTG |
| Lysine | Lys | K | AAA, AAG |
| Methionine | Met | M | ATG |
| Phenylalanine | Phe | F | TTC, TTT |
| Proline | Pro | P | CCA, CCC, CCG, CCT |
| Serine | Ser | S | AGC, AGT, TCA, TCC, TCG, TCT |
| Threonine | Thr | T | ACA, ACC, ACG, ACT |
| Tryptophan | Trp | W | TGG |
| Tyrosine | Tyr | Y | TAC TAT |
| Valine | Val | V | GTA, GTC, GTG, GTT |

In a further embodiment, the variant polypeptide having lipase activity is a "mature polypeptide." A mature polypeptide means an enzyme in its final form including any post-translational modifications, glycosylation, phosphorylation, truncation, N-terminal modifications, C-terminal modifications, signal sequence deletion. A mature polypeptide can vary depending upon the expression system, vector, promoter, and/or production process.

In a further embodiment, a lipase is active over a broad pH at any single point within the range from about pH 4.0 to about pH 12.0. In an embodiment, the lipase is active over a range of pH 4.0 to pH 11.0, pH 4.0 to pH 10.0, pH 4.0 to pH 9.0, pH 4.0 to pH 8.0, pH 4.0 to pH 7.0, pH 4.0 to pH 6.0, or pH 4.0 to pH 5.0. In another embodiment the lipase is active at pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6 pH 8.7, pH 8.8 pH 8.9, pH 9.0, pH 9.1, pH 9.2, pH 9.3, pH 9.4, pH 9.5, pH 9.6, pH 9.7, pH 9.8, pH 9.9, pH 10.0, pH 10.1, pH 10.2, pH 10.3, pH 10.4, pH 10.5, pH 10.6, pH 10.7, pH 10.8, pH 10.9, pH 11.0, pH 11.1, pH 11.2, pH 11.3, pH 11.4, pH 11.5, pH 11.6, pH 11.7, pH 11.8, pH 11.9, pH 12.0, pH 12.1, pH 12.2, pH 12.3, pH 12.4, and pH 12.5, pH 12.6, pH 12.7, pH 12.8, pH 12.9, and higher.

In a further embodiment, a lipase is active over a broad temperature used in at any time during a baking process, wherein the temperature is any point in the range from about 20° C. to about 60° C. In another embodiment, the lipase is active at a temperature range from 20° C. to 55° C., 20° C. to 50° C., 20° C. to 45° C., 20° C. to 40° C., 20° C. to 35° C., 20° C. to 30° C., or 20° C. to 25° C. In another embodiment the lipase is active at a temperature of at least 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., or higher temperatures.

"Sequence Identity," "% sequence identity." "% identity," or "Sequence alignment" means a comparison of a first amino acid sequence to a second amino acid sequence, or a comparison of a first nucleic acid sequence to a second nucleic acid sequence and is calculated as a percentage based on the comparison. The result of this calculation can be described as "percent identical" or "percent ID."

Generally, a sequence alignment can be used to calculate the sequence identity by one of two different approaches. In the first approach, both, mismatches at a single position and gaps at a single position are counted as non-identical positions in final sequence identity calculation. In the second approach, mismatches at a single position are counted as non-identical positions in final sequence identity calculation; however, gaps at a single position are not counted (ignored) as non-identical positions in final sequence identity calculation. In other words, in the second approach gaps are ignored in final sequence identity calculation. The differences between these two approaches, counting gaps as non-identical positions vs ignoring gaps, at a single position can lead to variability in sequence identity value between two sequences.

In an embodiment of this disclosure, sequence identity is determined by a program, which produces an alignment, and calculates identity counting both mismatches at a single position and gaps at a single position as non-identical positions in final sequence identity calculation. For example program Needle (EMBOS), which has implemented the algorithm of Needleman and Wunsch (Needleman and Wunsch, 1970, J. Mol. Biol. 48: 443-453), and which calculates sequence identity by first producing an alignment between a first sequence and a second sequence, then counting the number of identical positions over the length of the alignment, then dividing the number of identical residues by the length of an alignment, then multiplying this number by 100 to generate the % sequence identity [% sequence identity=(# of Identical residues/length of alignment)×100)].

In another embodiment of this disclosure, sequence identity can be calculated from a pairwise alignment showing both sequences over the full length, so showing the first sequence and the second sequence in their full length ("Global sequence identity"). For example, program Needle (EMBOSS) produces such alignments; % sequence identity=(# of identical residues/length of alignment)×100)].

In another embodiment of this disclosure, sequence identity can be calculated from a pairwise alignment showing only a local region of the first sequence or the second sequence ("Local Identity"). For example, program Blast (NCBI) produces such alignments; % sequence identity=(# of Identical residues/length of alignment)×100)].

In another embodiment, a sequence alignment is calculated with mismatches at a single position are counted as non-identical positions in final sequence identity calculation; however, gaps at a single position are not counted (ignored) as non-identical positions in final sequence identity calculation.

In a preferred embodiment the sequence alignment is generated by using the algorithm of Needleman and Wunsch (J. Mol. Biol. (1979) 48, p. 443-453). Preferably, the program "NEEDLE" (The European Molecular Biology Open Software Suite (EMBOSS)) is used for the purposes of the current invention, with using the programs default parameter (gap open=10.0, gap extend=0.5 and matrix= EBLOSUM62). Then, a sequence identity can be calculated from the alignment showing both sequences over the full length, so showing the first sequence and the second sequence in their full length ("Global sequence identity"). For example, % sequence identity=(# of identical residues/length of alignment)×100)].

In another preferred embodiment the preferred alignment program is "NEEDLE" with using the programs default parameter (gap open=10.0, gap extend=0.5 and matrix=EDNAFULL).

According to this invention, enzyme variants may be described as an amino acid sequence which is at least n % identical to the amino acid sequence of the respective parent enzyme with "n" being an integer between 10 and 100. In one embodiment, variant enzymes are at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical when compared to the full length amino acid sequence of the parent enzyme, wherein the enzyme variant has enzymatic activity.

The invention further relates to a polynucleotide encoding the variant polypeptides of the invention. The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length. A "gene" is a DNA segment carrying a certain genetic information.

A "parent" or "template nucleic acid sequence" is a polynucleotide acid sequence is the starting sequence for introduction of mutations to the sequence, resulting in "variants" of said parent polynucleotide sequence. A "variant polynucleotide" refers to a polynucleotide that encodes the same enzyme as the parent polynucleotide does. The variant polynucleotide in this case differs from its parent polynucleotide in its nucleic acid sequence, however the polypeptide encoded remains unchanged.

In an embodiment of the disclosure, the lipase can be used in combination with at least one other enzyme. The other enzyme can be from the same class of enzymes, for example, a composition comprising a first lipase and a second lipase. The other enzyme can also be from a different class of enzymes, for example, a composition comprising a lipase and an amylase. The combination with at least one other enzyme can be a composition comprising at least three enzymes. The three enzymes can have enzymes from the same class of enzymes, for example a first lipase, a second lipase, and a third lipase or the enzymes can be from different class of enzymes for example, a lipase, an amylase, and a xylanase. In another embodiment, the second enzyme comprises or is selected from the group consisting of: an Alpha-amylase; a beta-amylase a Glucan 1, 4-alpha-maltotetraohydrolase, also known as exo-maltotetraohydrolase, G4-amylase; a Glucan 1,4-alpha-maltohydrolase, also known as maltogenic alpha-amylase, a cyclodextrin glucanotransferase, a glucoamylase; an Endo-1,4-beta-xylanase; a xylanase, a cellulase, an Oxidoreductases; a Phospholipase A1; a Phospholipase A2; a Phospholipase C; a Phospholipase D; a Galactolipase, triacylglycerol lipase, an arabinofuranosidase, a transglutaminase, a pectinase, a pectate lyase, a a protease, or any combination thereof. In another embodiment, the enzyme combination is the lipase disclosed herein and a maltogenic alpha-amylase, or the enzyme combination is the lipase disclosed herein, a maltogenic alpha-amylase, and a xylanase.

In another embodiment of the disclosure, the lipase can be a hybrid of more than one lipase enzymes. A "hybrid" or "chimeric" or "fusion protein" means that a domain of a first lipase of the disclosure is combined with a domain of a second lipase to form a hybrid lipase and the hybrid has lipase activity. In one embodiment a domain of a lipase of this disclosure is combined with a domain of a commercially available lipase, such as LIPOPAN (available from Novozymes), or PANAMORE (available from DSM) to form a hybrid lipase and the hybrid has lipase activity.

Industrial enzymes are usually recombinant proteins produced using bacteria, fungi, or yeast expression systems. "Expression system" also means a host microorganism, expression hosts, host cell, production organism, or production strain and each of these terms can be used interchangeably for this disclosure. Examples of expression systems include but are not limited to: *Aspergillus niger, Aspergillus oryzae, Hansenula polymorpha, Thermomyces lanuginosus, Fusarium oxysporum, Fusarium heterosporum, Escherichia coli, Bacillus*, preferably *Bacillus subtilis*, or *Bacillus licheniformis, Pseudomonas*, preferably *Pseudomonas fluorescens, Pichia pastoris* (also known as *Komagataella phaffii*), *Thermothelomyces thermophila* (also known as *Myceliopthora thermophile* (C1)), *Schizosaccharomyces pombe, Trichoderma*, preferably *Trichoderma reesei* and *Saccharomyces*, preferably *Saccharomyces cerevisiae*. In an embodiment the lipase of this disclosure is produced using the expression system listed above.

Lipases are known to be useful for other industrial applications. In an embodiment of this disclosure, the lipase is used in a detergent. In an embodiment of this disclosure, the lipase is used in personal care products such as contact lens solution. In another embodiment, the lipase of this disclosure is used in the processing of textiles such as leather manufacturing. In another embodiment, the lipase of this disclosure can be used in pulp and paper processing. In a further embodiment, the pulp and paper processing is pitch control, or deinking. In another embodiment, a lipase of this disclosure can be used for manufacturing biodiesel. In another embodiment, a lipase of this disclosure can be used for cheese ripening. In another embodiment, lipases of this disclosure can be used in preparing a meat flavor and/or aroma. In another embodiment, a lipase of this disclosure can be used in the modification of oils & fats. In another embodiment, a lipase of this disclosure can be used in enzymatic oil degumming. In another embodiment, a lipase of this disclosure can be used in the production of ethanol.

The term "baked products" as used herein includes baked products such as bread, loaf bread, pan bread, crispy rolls, sandwich bread, buns, baguette, ciabatta, croissants, noodles, as well as fine bakery wares like donuts, brioche, stollen, cakes, muffins, etc.

The term "dough" as used herein is defined as a mixture of flour, salt, yeast and water, which can be kneaded, molded, shaped or rolled prior to baking. In addition, also other ingredients such as sugar, margarine, egg, milk, etc. might be used. The term includes doughs used for the preparation of baked goods, such as bread, rolls, sandwich bread, baguette, ciabatta, croissants, sweet yeast doughs, etc.

The term "bread volume" as used herein is the volume of a baked good determined by using a laser scanner (e.g. Volscan Profiler ex Micro Stable System) to measure the volume as well as the specific volume. The term also includes the volume which is determined by measuring the length, the width and the height of certain baked goods.

The term "comprising" as used herein is synonymous with "including," "containing," or "characterized by," and is inclusive or open-ended and does not exclude additional, unrecited elements or method steps.

It is understood that aspects and embodiments of the invention described herein include "consisting" and/or "consisting essentially of" aspects and embodiments.

Throughout this disclosure, various aspects are presented in a range format. It should be understood the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present disclosure will become apparent from the following specifications taken in conjunction with the accompanying drawings.

In the following description, numerous specific details are set forth to provide a more thorough understanding of the present disclosure. However, it will be apparent to one of skill in the art that the methods of the present disclosure may be practiced without one or more of these specific details. In other instances, well-known features and procedures well known to those skilled in the art have not been described to avoid obscuring the disclosure.

Example 1

Variant Lipase Enzymes

Non-naturally occurring variant lipase enzymes were created in a lab using rational design single site mutagenesis and multisite mutagenesis. The variant lipase enzymes include single point amino acid modifications, insertions, or deletions of a parent enzyme (LIP062, which is the amino acid sequence of SEQ ID 1, and is encoded by nucleic acid sequence of SEQ ID NO:2) at 18 different amino acid residue positions: 23, 33, 82, 83, 84, 85, 160, 199, 254, 255, 256, 258, 263, 264, 265, 268, 308, 311, or any combination thereof, wherein the variant lipase enzymes has lipase activity.

Variant lipase enzymes were also created with various combinations of the single point modifications of a parent enzyme (LIP062), wherein the variant lipase enzymes have lipase activity. For example, the single point modifications and various combinations of single point modifications are listed in Table: 1.

The table shows a variant lipase enzyme of LIP096, which is a variant polypeptide having the amino acid sequence of LIP062 and one amino acid substitution of A256D, wherein the variant polypeptide has lipase activity. This table also shows a variant lipase enzyme of LIP182, which is a variant polypeptide having an amino acid sequence of LIP062 and a combination of amino acid substitutions of S83H, I85S, I255A, T264A, and D265T, wherein the variant polypeptide has lipase activity. Table 1, also shows lipase variants of the parent lipase, wherein the variant includes an insertion of an amino acid residue. The insertion of an amino acid residue is shown as ('), for example (84')

TABLE 1

| | Amino Acid Residue Position Numbers | | | | | | | | | | | | | | | | | |
|---|---|---|---|---|---|---|---|---|---|---|---|---|---|---|---|---|---|---|
| | 23 | 33 | 82 | 83 | 84 | 84' | 85 | 160 | 199 | 254 | 255 | 256 | 258 | 263 | 264 | 265 | 268 | 308 | 311 |
| | | | | | | | | | | | LIP062 | | | | | | | | |
| Lipase | Y | K | S | S | N | — | I | K | P | I | I | A | L | D | T | D | T | D | Y |
| LIP182 | — | — | — | H | — | — | S | — | — | — | A | — | — | — | A | T | — | — | — |
| LIP181 | — | — | — | H | — | — | V | — | — | — | A | — | — | — | S | T | — | — | — |
| LIP180 | — | — | — | T | — | — | H | — | — | — | A | — | — | — | — | A | — | — | — |
| LIP179 | — | — | — | — | — | — | V | — | — | — | A | — | — | — | S | T | — | — | — |
| LIP178 | — | — | — | H | — | — | L | — | — | — | A | — | — | — | S | A | — | — | — |
| LIP177 | — | — | — | H | — | — | T | — | — | — | A | — | — | — | — | T | — | — | — |
| LIP176 | — | — | — | Y | — | — | A | — | — | — | A | — | — | — | — | T | — | — | — |
| LIP175 | — | — | — | T | — | — | V | — | — | — | A | — | — | — | — | S | — | — | — |
| LIP174 | — | — | — | — | — | — | — | — | — | — | A | — | — | — | — | A | — | — | — |
| LIP173 | — | — | — | — | — | — | — | — | — | — | A | — | — | — | — | S | — | — | — |
| LIP172 | — | — | — | N | — | — | L | — | — | — | A | — | — | — | N | T | — | — | — |
| LIP171 | — | — | — | — | — | — | — | — | — | — | A | — | — | — | D | T | — | — | — |
| LIP170 | — | — | — | N | — | — | L | — | — | — | A | — | — | — | — | T | — | — | — |
| LIP169 | — | — | — | N | — | — | V | — | — | L | — | — | — | — | S | T | — | — | — |
| LIP168 | — | — | — | H | — | — | — | — | — | L | — | — | — | — | A | A | — | — | — |
| LIP167 | — | — | — | H | — | — | — | — | — | L | — | — | — | — | — | T | — | — | — |
| LIP166 | — | — | — | — | — | — | V | — | — | L | — | — | — | — | D | T | — | — | — |
| LIP165 | — | — | — | Y | — | — | — | — | — | — | — | — | — | — | A | T | — | — | — |
| LIP164 | — | — | — | — | — | — | V | — | — | — | — | — | — | — | D | T | — | — | — |
| LIP163 | — | — | — | Y | — | — | A | — | — | — | — | — | — | — | A | T | — | — | — |
| LIP162 | — | — | — | N | — | — | V | — | — | — | — | — | — | — | N | T | — | — | — |
| LIP161 | — | — | — | N | — | — | — | — | — | — | — | — | — | — | D | T | — | — | — |
| LIP160 | — | — | — | H | — | — | L | — | — | — | — | — | — | — | — | T | — | — | — |
| LIP159 | — | — | — | H | — | — | A | — | — | — | — | — | — | — | A | T | — | — | — |
| LIP158 | — | — | — | T | — | — | V | — | — | — | — | — | — | — | — | T | — | — | — |
| LIP157 | — | — | — | H | — | — | L | — | — | — | — | — | — | — | — | A | — | — | — |
| LIP156 | — | — | — | H | — | — | V | — | — | — | — | — | — | — | — | A | — | — | — |
| LIP155 | — | — | — | T | — | — | A | — | — | — | — | — | — | — | — | T | — | — | — |
| LIP154 | — | — | — | H | — | — | V | — | — | — | — | — | — | — | N | T | — | — | — |
| LIP153 | — | — | — | — | — | — | V | — | — | — | — | — | — | — | — | G | — | — | — |
| LIP152 | — | — | — | H | — | — | — | — | — | — | — | — | — | — | — | A | — | — | — |
| LIP151 | — | — | — | Y | — | — | V | — | — | — | — | — | — | — | S | S | — | — | — |
| LIP150 | — | — | — | N | — | — | V | — | — | — | — | — | — | — | — | G | — | — | — |
| LIP149 | — | — | — | H | — | — | — | — | — | — | — | — | — | — | — | S | — | — | — |
| LIP148 | — | — | — | H | — | — | — | — | — | — | — | — | — | — | — | G | — | — | — |
| LIP147 | — | — | — | H | — | — | — | — | — | — | — | — | — | — | — | S | G | — | — |
| LIP146 | — | — | — | H | — | — | — | — | — | — | — | — | — | — | — | G | G | — | — |
| LIP145 | — | — | — | — | — | — | — | — | — | — | A | — | — | — | — | S | G | — | — |
| LIP144 | — | — | — | H | — | — | — | — | — | — | A | — | — | — | — | G | — | — | — |
| LIP143 | — | — | — | H | — | — | — | — | — | — | A | — | — | — | — | S | G | — | — |
| LIP142 | — | — | — | H | — | — | — | — | — | — | A | — | — | — | — | G | G | — | — |
| LIP135 | — | — | — | — | — | — | — | — | — | — | L | — | — | — | — | — | — | — | — |
| LIP134 | — | — | — | — | — | — | — | — | — | — | A | — | — | — | — | — | — | — | — |
| LIP131 | — | — | — | I | — | — | L | — | — | — | — | — | — | — | — | S | — | — | — |
| LIP130 | — | — | — | I | — | — | L | — | — | — | — | — | — | — | — | G | — | — | — |
| LIP126 | — | — | — | — | — | — | — | — | — | — | — | — | — | R | — | — | — | — | — |
| LIP124 | — | — | — | — | — | — | T | — | — | — | — | — | — | — | — | G | G | — | — |
| LIP123 | — | — | — | — | — | — | L | — | — | — | — | — | — | — | — | G | G | — | — |
| LIP120 | — | — | — | H | — | — | L | — | — | — | — | — | — | — | — | — | G | — | — |
| LIP119 | — | — | — | — | — | — | T | — | — | — | — | — | — | — | — | S | G | — | — |
| LIP118 | — | — | — | H | — | — | L | — | — | — | — | — | — | — | — | G | — | — | — |
| LIP117 | — | — | — | H | — | — | T | — | — | — | — | — | — | — | — | S | G | — | — |
| LIP116 | — | — | — | H | — | — | L | — | — | — | — | — | — | — | — | G | G | — | — |
| LIP115 | — | — | — | H | — | — | L | — | — | — | — | — | — | — | — | S | G | — | — |
| LIP114 | — | — | — | H | — | — | L | — | — | — | — | — | — | — | — | S | — | — | — |
| LIP113 | — | — | — | — | — | — | L | — | — | — | — | — | — | — | — | S | G | — | — |
| LIP111 | — | — | — | — | — | — | — | — | — | — | — | — | — | — | — | A | — | — | — |
| LIP110 | — | — | — | — | — | — | — | — | — | — | — | — | — | — | — | S | — | — | — |
| LIP109 | — | — | — | — | — | — | — | — | — | — | — | — | — | — | — | G | — | — | — |
| LIP108 | — | — | — | H | — | — | — | — | — | — | — | — | — | — | — | — | — | — | — |
| LIP102 | — | — | — | — | — | — | T | — | — | — | — | — | — | — | — | — | — | — | — |
| LIP101 | — | — | — | — | — | — | P | — | — | — | — | — | — | — | — | — | — | — | — |
| LIP100 | — | — | — | — | — | — | L | — | — | — | — | — | — | — | — | — | — | — | — |
| LIP099 | — | — | — | — | — | — | A | — | — | — | — | — | — | — | — | — | — | — | — |
| LIP096 | — | — | — | — | — | — | — | — | — | — | — | D | — | — | — | — | — | — | — |
| LIP095 | — | — | — | — | — | — | — | N | — | — | — | — | — | — | — | — | — | — | — |
| LIP094 | — | N | — | — | — | — | — | — | — | — | — | — | — | — | — | — | — | — | — |
| LIP090 | — | — | — | — | — | — | — | — | V | — | — | — | — | — | — | — | — | — | — |
| LIP089 | — | T | — | — | — | — | — | — | — | — | — | — | — | — | — | — | — | — | — |
| LIP062_1909 | — | — | — | — | — | — | T | — | — | — | A | — | — | — | — | — | — | — | — |
| LIP062_1908 | — | — | — | H | — | — | T | — | — | — | A | — | — | — | — | — | — | — | — |
| LIP062_1907 | — | — | — | — | — | — | P | — | — | — | A | — | — | — | — | S | — | — | — |
| LIP062_1906 | — | — | — | H | — | — | P | — | — | — | A | — | — | — | — | — | — | — | — |

TABLE 1-continued

| | Amino Acid Residue Position Numbers | | | | | | | | | | | | | | | | | |
|---|---|---|---|---|---|---|---|---|---|---|---|---|---|---|---|---|---|---|
| | 23 | 33 | 82 | 83 | 84 | 84' | 85 | 160 | 199 | 254 | 255 | 256 | 258 | 263 | 264 | 265 | 268 | 308 | 311 |
| | | | | | | | | | | | LIP062 | | | | | | | | |
| Lipase | Y | K | S | S | N | — | I | K | P | I | I | A | L | D | T | D | T | D | Y |
| LIP062_1905 | — | — | — | I | — | — | — | — | — | — | A | — | — | — | — | G | G | — | — |
| LIP062_1904 | — | — | — | — | — | — | — | — | — | — | A | — | — | — | — | G | G | — | — |
| LIP062_1903 | — | — | — | H | — | — | P | — | — | — | — | — | — | — | — | — | G | — | — |
| LIP062_1902 | — | — | — | — | — | — | P | — | — | — | — | — | — | — | — | S | G | — | — |
| LIP062_1901 | — | — | — | — | — | — | T | — | — | — | — | — | — | — | — | S | — | — | — |
| LIP062_1900 | — | — | — | H | — | — | T | — | — | — | — | — | — | — | — | — | — | — | — |
| LIP062_1899 | — | — | — | — | — | — | P | — | — | — | — | — | — | — | — | S | — | — | — |
| LIP062_1898 | — | — | — | H | — | — | P | — | — | — | — | — | — | — | — | — | — | — | — |
| LIP062_1897 | — | — | — | I | — | — | — | — | — | — | — | — | — | — | — | G | — | — | — |
| LIP062_1896 | — | — | — | — | — | — | — | — | — | — | — | — | — | — | — | S | G | — | — |
| LIP062_1895 | — | — | — | I | — | — | — | — | — | — | — | — | — | — | — | G | G | — | — |
| LIP062_1894 | — | — | — | — | — | — | — | — | — | — | — | — | — | — | — | G | G | — | — |
| LIP062_1893 | — | — | — | I | — | — | T | — | — | — | — | — | — | — | — | — | G | — | — |
| LIP062_1892 | — | — | — | H | — | — | T | — | — | — | — | — | — | — | — | — | G | — | — |
| LIP062_1891 | — | — | — | I | — | — | T | — | — | — | — | — | — | — | — | S | — | — | — |
| LIP062_1890 | — | — | — | I | — | — | T | — | — | — | — | — | — | — | — | G | — | — | — |
| LIP062_1889 | — | — | — | H | — | — | T | — | — | — | — | — | — | — | — | S | — | — | — |
| LIP062_1888 | — | — | — | H | — | — | T | — | — | — | — | — | — | — | — | G | — | — | — |
| LIP062_1887 | — | — | — | I | — | — | L | — | — | — | — | — | — | — | — | — | G | — | — |
| LIP062_1886 | — | — | — | I | — | — | T | — | — | — | — | — | — | — | — | S | G | — | — |
| LIP062_1885 | — | — | — | I | — | — | L | — | — | — | — | — | — | — | — | S | G | — | — |
| LIP062_1884 | — | — | — | I | — | — | T | — | — | — | — | — | — | — | — | G | G | — | — |
| LIP062_1883 | — | — | — | I | — | — | L | — | — | — | — | — | — | — | — | G | G | — | — |
| LIP062_1882 | — | — | — | H | — | — | T | — | — | — | — | — | — | — | — | G | G | — | — |
| LIP062_1881 | — | — | — | — | — | — | — | — | — | — | — | — | — | — | I | — | — | — | — |
| LIP062_1880 | — | — | — | — | — | — | — | — | — | — | — | — | — | — | L | — | — | — | — |
| LIP062_1879 | — | — | — | — | — | — | — | — | — | — | — | — | — | P | — | — | — | — | — |
| LIP062_1878 | — | — | — | — | — | — | — | — | — | — | — | — | — | G | — | — | — | — | — |
| LIP062_1877 | — | — | — | — | — | — | — | — | — | — | — | — | — | S | — | — | — | — | — |
| LIP062_1876 | — | — | — | — | — | — | — | — | — | — | — | — | — | K | — | — | — | — | — |
| LIP062_1875 | — | — | — | I | N | — | V | — | — | — | — | — | — | — | — | — | — | — | — |
| LIP062_1874 | — | — | — | R | S | — | V | — | — | — | — | — | — | — | — | — | — | — | — |
| LIP062_1873 | — | — | — | — | — | — | — | — | — | — | — | — | — | — | — | — | L | — | — |
| LIP062_1872 | — | — | — | — | — | — | — | — | — | — | — | — | — | — | — | — | A | — | — |
| LIP062_1871 | — | — | — | — | — | — | — | — | — | — | — | — | — | — | — | — | N | — | — |
| LIP062_1870 | — | — | — | — | — | — | — | — | — | — | — | — | — | — | — | — | K | — | — |
| LIP062_1869 | — | — | — | — | — | — | — | — | — | — | — | — | — | — | — | — | S | — | — |
| LIP062_1868 | — | — | — | — | — | — | — | — | — | — | — | — | — | — | — | — | G | — | — |
| LIP062_1867 | — | — | — | — | — | — | — | — | — | — | — | — | — | — | — | L | — | — | — |
| LIP062_1866 | — | — | — | — | — | — | — | — | — | — | — | — | — | — | — | N | — | — | — |
| LIP062_1865 | — | — | — | — | — | — | — | — | — | — | — | — | — | — | — | K | — | — | — |
| LIP062_1864 | — | — | — | N | — | — | — | — | — | — | — | — | — | — | — | — | — | — | — |
| LIP062_1863 | — | — | — | D | — | — | — | — | — | — | — | — | — | — | — | — | — | — | — |
| LIP062_1862 | — | — | — | I | — | — | — | — | — | — | — | — | — | — | — | — | — | — | — |
| LIP062_1861 | A | — | — | — | — | — | — | — | — | — | — | — | — | — | — | — | — | — | — |
| LIP062_1860 | — | — | — | — | — | — | — | — | — | — | — | — | — | — | — | — | — | A | E |
| LIP062_1859 | — | — | — | — | — | — | — | — | — | — | — | — | — | — | — | — | — | A | — |
| LIP062_1858 | — | — | — | — | — | — | — | — | — | — | — | — | — | — | — | — | — | — | E |
| LIP062_1857 | — | — | — | — | S | — | — | — | — | — | — | — | — | — | — | — | — | — | — |
| LIP062_1856 | — | — | — | — | L | — | — | — | — | — | — | — | — | — | — | — | — | — | — |
| LIP062_1855 | — | — | — | — | Y | — | — | — | — | — | — | — | — | — | — | — | — | — | — |
| LIP062_1854 | — | — | — | — | — | — | — | — | — | — | — | — | E | — | — | — | — | — | — |
| LIP062_1853 | — | — | — | — | — | — | — | — | — | — | — | — | Q | — | — | — | — | — | — |
| LIP062_1852 | — | — | — | — | — | — | — | — | — | — | — | — | T | — | — | — | — | — | — |
| LIP062_1851 | — | — | — | — | — | — | — | — | — | — | — | — | H | — | — | — | — | — | — |
| LIP062_1850 | — | — | — | — | — | — | — | — | — | — | — | — | D | — | — | — | — | — | — |
| LIP062_1849 | — | — | — | — | — | — | — | — | — | — | — | — | V | — | — | — | — | — | — |
| LIP062_1848 | — | — | — | — | — | — | — | — | — | — | — | — | R | — | — | — | — | — | — |
| LIP062_1847 | — | — | — | — | — | — | — | — | — | — | — | — | N | — | — | — | — | — | — |
| LIP062_1846 | — | — | — | — | — | — | — | — | — | — | — | — | G | — | — | — | — | — | — |
| LIP062_1845 | — | — | — | — | — | — | — | — | — | — | — | — | A | — | — | — | — | — | — |
| LIP062_1844 | — | — | — | — | — | — | — | — | — | — | — | — | S | — | — | — | — | — | — |
| LIP062_1843 | — | — | — | — | — | — | — | — | — | M | — | — | — | — | — | — | — | — | — |
| LIP062_1842 | — | — | — | — | — | — | — | — | — | G | — | — | — | — | — | — | — | — | — |
| LIP062_1841 | — | — | — | — | — | — | — | — | — | R | — | — | — | — | — | — | — | — | — |
| LIP062_1840 | — | — | — | — | — | — | — | — | — | F | — | — | — | — | — | — | — | — | — |
| LIP062_1839 | — | — | — | — | — | — | — | — | — | E | — | — | — | — | — | — | — | — | — |
| LIP062_1838 | — | — | — | — | — | — | — | — | — | W | — | — | — | — | — | — | — | — | — |
| LIP062_1837 | — | — | — | — | — | — | — | — | — | L | — | — | — | — | — | — | — | — | — |
| LIP062_1836 | — | — | — | — | — | — | — | — | — | Y | — | — | — | — | — | — | — | — | — |
| LIP062_1835 | — | — | — | — | — | — | — | — | — | S | — | — | — | — | — | — | — | — | — |
| LIP062_1834 | — | — | — | — | — | — | — | — | — | C | — | — | — | — | — | — | — | — | — |
| LIP062_1833 | — | — | — | — | — | — | — | — | — | A | — | — | — | — | — | — | — | — | — |

TABLE 1-continued

| | Amino Acid Residue Position Numbers | | | | | | | | | | | | | | | | | | |
|---|---|---|---|---|---|---|---|---|---|---|---|---|---|---|---|---|---|---|---|
| | 23 | 33 | 82 | 83 | 84 | 84' | 85 | 160 | 199 | 254 | 255 | 256 | 258 | 263 | 264 | 265 | 268 | 308 | 311 |
| | | | | | | | | | | LIP062 | | | | | | | | | |
| Lipase | Y | K | S | S | N | — | I | K | P | I | I | A | L | D | T | D | T | D | Y |
| LIP062_1832 | — | — | — | — | — | — | — | — | — | V | — | — | — | — | — | — | — | — | — |
| LIP062_1831 | — | — | — | — | — | — | — | — | — | N | — | — | — | — | — | — | — | — | — |
| LIP062_1830 | — | — | — | — | — | — | M | — | — | — | — | — | — | — | — | — | — | — | — |
| LIP062_1829 | — | — | — | — | — | — | S | — | — | — | — | — | — | — | — | — | — | — | — |
| LIP062_1828 | — | — | — | — | — | — | C | — | — | — | — | — | — | — | — | — | — | — | — |
| LIP062_1827 | — | N | — | — | — | — | — | N | — | — | — | — | — | — | — | — | — | — | — |
| LIP062_1826 | — | — | — | — | — | — | — | — | I | — | — | — | — | — | — | — | — | — | — |
| LIP062_1825 | — | — | — | N | — | — | V | — | — | — | A | — | — | — | A | G | — | — | — |
| LIP062_1824 | — | — | — | T | — | — | V | — | — | — | A | — | — | — | — | G | — | — | — |
| LIP062_1823 | — | — | — | N | — | — | V | — | — | — | A | — | — | — | S | S | — | — | — |
| LIP062_1822 | — | — | — | H | — | — | T | — | — | — | A | — | — | — | S | S | — | — | — |
| LIP062_1820 | — | — | — | — | — | — | — | — | — | — | A | — | — | — | A | T | — | — | — |
| LIP062_1818 | — | — | — | Y | — | — | — | — | — | — | A | — | — | — | — | T | — | — | — |
| LIP062_1817 | — | — | — | — | — | — | — | — | — | — | A | — | — | — | G | T | — | — | — |
| LIP062_1816 | — | — | — | — | — | — | — | — | — | — | A | — | — | — | N | A | — | — | — |
| LIP062_1814 | — | — | — | T | — | — | A | — | — | — | A | — | — | — | — | T | — | — | — |
| LIP062_1812 | — | — | — | N | — | — | — | — | — | — | A | — | — | — | — | A | — | — | — |
| LIP062_1810 | — | — | — | T | — | — | — | — | — | — | A | — | — | — | N | T | — | — | — |
| LIP062_1807 | — | — | — | — | — | — | — | — | — | — | A | — | — | — | D | A | — | — | — |
| LIP062_1805 | — | — | — | H | — | — | V | — | — | — | A | — | — | — | — | A | — | — | — |
| LIP062_1804 | — | — | — | H | — | — | — | — | — | — | A | — | — | — | A | T | — | — | — |
| LIP062_1803 | — | — | — | N | — | — | V | — | — | — | A | — | — | — | S | A | — | — | — |
| LIP062_1801 | — | — | — | — | — | — | — | — | — | — | A | — | — | — | — | G | — | — | — |
| LIP062_1799 | — | — | — | — | — | — | — | — | — | — | A | — | — | — | N | T | — | — | — |
| LIP062_1798 | — | — | — | Y | — | — | V | — | — | — | A | — | — | — | N | T | — | — | — |
| LIP062_1797 | — | — | — | H | — | — | T | — | — | — | A | — | — | — | — | A | — | — | — |
| LIP062_1796 | — | — | — | H | — | — | — | — | — | — | A | — | — | — | A | S | — | — | — |
| LIP062_1795 | — | — | — | N | — | — | V | — | — | — | A | — | — | — | N | T | — | — | — |
| LIP062_1793 | — | — | — | — | — | — | — | — | — | — | A | — | — | — | — | T | — | — | — |
| LIP062_1792 | — | — | — | Y | — | — | V | — | — | — | A | — | — | — | S | T | — | — | — |
| LIP062_1790 | — | — | — | — | — | — | — | — | — | — | A | — | — | — | S | S | — | — | — |
| LIP062_1788 | — | — | — | N | — | — | L | — | — | — | A | — | — | — | S | G | — | — | — |
| LIP062_1782 | — | — | — | N | — | — | — | — | — | L | — | — | — | — | N | T | — | — | — |
| LIP062_1781 | — | — | — | H | — | — | A | — | — | L | — | — | — | — | A | T | — | — | — |
| LIP062_1780 | — | — | — | H | — | — | — | — | — | L | — | — | — | — | — | G | — | — | — |
| LIP062_1779 | — | — | — | N | — | — | V | — | — | L | — | — | — | — | D | T | — | — | — |
| LIP062_1778 | — | — | — | — | — | — | — | — | — | L | — | — | — | — | A | T | — | — | — |
| LIP062_1776 | — | — | — | H | — | — | V | — | — | L | — | — | — | — | — | A | — | — | — |
| LIP062_1775 | — | — | — | T | — | — | V | — | — | L | — | — | — | — | S | A | — | — | — |
| LIP062_1774 | — | — | — | — | — | — | — | — | — | L | — | — | — | — | D | A | — | — | — |
| LIP062_1773 | — | — | — | N | — | — | V | — | — | L | — | — | — | — | A | A | — | — | — |
| LIP062_1770 | — | — | — | — | — | — | — | — | — | L | — | — | — | — | N | T | — | — | — |
| LIP062_1768 | — | — | — | — | — | — | — | — | — | L | — | — | — | — | D | T | — | — | — |
| LIP062_1767 | — | — | — | — | — | — | — | — | — | L | — | — | — | — | S | T | — | — | — |
| LIP062_1766 | — | — | — | — | — | — | — | — | — | L | — | — | — | — | N | A | — | — | — |
| LIP062_1704 | — | — | — | H | — | — | — | — | — | — | — | — | — | — | A | A | — | — | — |
| LIP062_1703 | — | — | — | H | — | — | T | — | — | — | — | — | — | — | A | A | — | — | — |
| LIP062_1701 | — | — | — | T | — | — | V | — | — | — | — | — | — | — | G | T | — | — | — |
| LIP062_1700 | — | — | — | — | — | — | — | — | — | — | — | — | — | — | S | T | — | — | — |
| LIP062_1696 | — | — | — | — | — | — | — | — | — | — | — | — | — | — | A | T | — | — | — |
| LIP062_1695 | — | — | — | N | — | — | V | — | — | — | — | — | — | — | A | T | — | — | — |
| LIP062_1694 | — | — | — | — | — | — | — | — | — | — | — | — | — | — | — | G | — | — | — |
| LIP062_1692 | — | — | — | — | — | — | — | — | — | — | — | — | — | — | A | T | — | — | — |
| LIP062_1691 | — | — | — | N | — | — | V | — | — | — | — | — | — | — | S | S | — | — | — |
| LIP062_1686 | — | — | — | H | — | — | V | — | — | — | — | — | — | — | A | S | — | — | — |
| LIP062_1685 | — | — | — | N | — | — | V | — | — | — | — | — | — | — | N | A | — | — | — |
| LIP062_1684 | — | — | — | — | — | — | — | — | — | — | — | — | — | — | N | T | — | — | — |
| LIP062_1683 | — | — | — | — | — | — | — | — | — | — | — | — | — | — | D | A | — | — | — |
| LIP062_1681 | — | — | — | T | — | — | — | — | — | — | — | — | — | — | N | T | — | — | — |
| LIP062_1680 | — | — | — | N | — | — | A | — | — | — | — | — | — | — | — | T | — | — | — |
| LIP062_1678 | — | — | — | N | — | — | — | — | — | — | — | — | — | — | — | A | — | — | — |
| LIP062_1677 | — | — | — | — | — | — | — | — | — | — | — | — | — | — | G | T | — | — | — |
| LIP062_1676 | — | — | — | Y | — | — | — | — | — | — | — | — | — | — | G | T | — | — | — |
| LIP062_1674 | — | — | — | — | — | — | — | — | — | — | — | — | — | — | G | T | — | — | — |
| LIP062_1670 | — | — | — | N | — | — | — | — | — | — | — | — | — | — | — | T | — | — | — |
| LIP062_1669 | — | — | — | — | — | — | — | — | — | — | — | — | — | — | S | G | — | — | — |
| LIP062_1668 | — | — | — | N | — | — | — | — | — | — | — | — | — | — | — | G | — | — | — |
| LIP062_1667 | — | — | — | — | — | — | A | — | — | — | — | — | — | — | — | G | — | — | — |
| LIP062_1665 | — | — | — | — | — | — | — | — | — | — | — | — | — | — | D | T | — | — | — |
| LIP062_1664 | — | — | — | N | — | — | — | — | — | L | — | — | — | — | A | T | — | — | — |

TABLE 1-continued

| | Amino Acid Residue Position Numbers | | | | | | | | | | | | | | | | | | |
|---|---|---|---|---|---|---|---|---|---|---|---|---|---|---|---|---|---|---|---|
| | 23 | 33 | 82 | 83 | 84 | 84' | 85 | 160 | 199 | 254 | 255 | 256 | 258 | 263 | 264 | 265 | 268 | 308 | 311 |
| | | | | | | | | | | | LIP062 | | | | | | | | |
| Lipase | Y | K | S | S | N | — | I | K | P | I | I | A | L | D | T | D | T | D | Y |
| LIP062_0450 | — | — | — | — | — | — | — | F | — | — | — | — | — | — | — | — | — | — | — |
| LIP062_0449 | — | — | — | — | — | — | — | Y | — | — | — | — | — | — | — | — | — | — | — |
| LIP062_0391 | — | — | — | — | — | — | — | — | — | — | — | — | — | — | — | — | — | — | — |

Example 2

Expression and Purification of Lipase Enzymes

Expression

The variant lipase enzymes were obtained by constructing expression plasmids containing the encoding polynucleotide sequences, transforming plasmids into *Pichia pastoris* (*Komagataella phaffii*) and growing the resulting expression strains in the following way. Fresh *Pichia pastoris* cells of the expression strains were obtained by spreading the glycerol stocks of sequence-confirmed strains onto Yeast extract Peptone Dextrose (YPD) agar plates containing Zeocin. After 2 days, starter seed cultures of the production strains were inoculated into 100 mL of Buffered Glycerol complex Medium (BMGY) using cells from these plates, and grown for 20-24 hours at 30° C. and 225-250 rpm. Seed cultures were scaled up by transferring suitable amounts into 2-4 L of BMMY medium in a baffled Fermentor. Fermentations were carried out at 30° C. and under 1100 rpm of agitation, supplied via flat-blade impellers, for 48-72 hours. After the initial batch-phase of fermentation, sterile-filtered Methanol was added as feed whenever the dissolved oxygen level in the culture dipped below 30%. Alternatively, feed was added every 3 hours at 0.5% v/v of the starting batch culture. The final fermentation broth was centrifuged at 7000×g for 30 mins at 4° C. to obtain the cell-free supernatant.

Expression levels of the variant lipase enzymes are shown in Table 2, determined as follows: supernatant was assayed for protein of interest expression by either SDS-PAGE or capillary electrophoresis and by enzymatic activity using PNP-octanoate as substrate. The results are shown below in Table 2, and the data is shown as a percentage as compared to the parent (LIP062) expression. The expression levels were not determined "n.d." for some of the variant lipase enzymes; however, enough material was generated to move the variant lipase enzyme into the Lipase Activity testing in Example 3, and sent for amino acid sequence identification as described above in Example 1, Table 1.

TABLE 2

| Lipase | Expression |
|---|---|
| LIP062 | 100 |
| LIP089 | 100 |
| LIP090 | 20 |
| LIP094 | 100 |
| LIP095 | 100 |
| LIP096 | 100 |
| LIP062_391 | 20 |
| LIP101 | 30 |
| LIP102 | 30 |
| LIP099 | 30 |
| LIP100 | 50 |
| LIP062_449 | 20 |
| LIP062_450 | 20 |
| LIP108 | 80 |
| LIP109 | 70 |
| LIP110 | 65 |
| LIP111 | 140 |
| LIP113 | 100 |
| LIP114 | 62 |
| LIP115 | 30 |
| LIP116 | 71 |
| LIP117 | 24 |
| LIP118 | 28 |
| LIP119 | 34 |
| LIP120 | 80 |
| LIP123 | 80 |
| LIP124 | 26 |
| LIP126 | 200 |
| LIP134 | 200 |
| LIP135 | 150 |
| LIP130 | 49 |
| LIP131 | 57 |
| LIP146 | n.d. |
| LIP147 | n.d. |
| LIP148 | n.d. |
| LIP149 | n.d. |
| LIP142 | 100 |
| LIP143 | 200 |
| LIP144 | 100 |
| LIP145 | 100 |
| LIP062_1664 | n.d. |
| LIP062_1665 | n.d. |
| LIP160 | n.d. |
| LIP062_1667 | n.d. |
| LIP062_1668 | n.d. |
| LIP062_1669 | n.d. |
| LIP062_1670 | n.d. |
| LIP161 | n.d. |
| LIP154 | 100 |
| LIP162 | n.d. |
| LIP062_1674 | n.d. |
| LIP163 | n.d. |
| LIP062_1676 | n.d. |
| LIP062_1677 | n.d. |
| LIP062_1678 | n.d. |
| LIP165 | n.d. |
| LIP062_1680 | n.d. |
| LIP062_1681 | n.d. |
| LIP150 | n.d. |
| LIP062_1683 | n.d. |
| LIP062_1684 | n.d. |
| LIP062_1685 | n.d. |
| LIP062_1686 | n.d. |
| LIP155 | n.d. |
| LIP151 | n.d. |
| LIP156 | n.d. |
| LIP153 | n.d. |
| LIP062_1691 | n.d. |
| LIP062_1692 | n.d. |
| LIP159 | n.d. |
| LIP062_1694 | n.d. |
| LIP062_1695 | n.d. |
| LIP062_1696 | n.d. |
| LIP157 | n.d. |
| LIP158 | n.d. |

TABLE 2-continued

| Lipase | Expression |
|---|---|
| LIP164 | n.d. |
| LIP062_1700 | n.d. |
| LIP062_1701 | n.d. |
| LIP152 | n.d. |
| LIP062_1703 | n.d. |
| LIP062_1704 | n.d. |
| LIP062_1766 | n.d. |
| LIP062_1767 | n.d. |
| LIP062_1768 | n.d. |
| LIP166 | n.d. |
| LIP062_1770 | n.d. |
| LIP167 | n.d. |
| LIP168 | n.d. |
| LIP062_1773 | n.d. |
| LIP062_1774 | n.d. |
| LIP062_1775 | n.d. |
| LIP062_1776 | n.d. |
| LIP169 | n.d. |
| LIP062_1778 | n.d. |
| LIP062_1779 | n.d. |
| LIP062_1780 | n.d. |
| LIP062_1781 | n.d. |
| LIP062_1782 | n.d. |
| LIP062_1788 | 100 |
| LIP170 | 100 |
| LIP062_1790 | 100 |
| LIP171 | 200 |
| LIP062_1792 | 200 |
| LIP062_1793 | 100 |
| LIP181 | 100 |
| LIP062_1795 | 100 |
| LIP062_1796 | 100 |
| LIP062_1797 | 100 |
| LIP062_1798 | 100 |
| LIP062_1799 | 200 |
| LIP172 | 50 |
| LIP062_1801 | 100 |
| LIP173 | 100 |
| LIP062_1803 | 100 |
| LIP062_1804 | 100 |
| LIP062_1805 | 100 |
| LIP174 | 200 |
| LIP062_1807 | 100 |
| LIP175 | 100 |
| LIP178 | 100 |
| LIP062_1810 | 200 |
| LIP176 | 100 |
| LIP062_1812 | 100 |
| LIP177 | 100 |
| LIP062_1814 | 100 |
| LIP179 | 100 |
| LIP062_1816 | 200 |
| LIP062_1817 | 100 |
| LIP062_1818 | 100 |
| LIP180 | 200 |
| LIP062_1820 | 100 |
| LIP182 | 50 |
| LIP062_1822 | 100 |
| LIP062_1823 | 100 |
| LIP062_1824 | 100 |
| LIP062_1825 | 100 |
| LIP062_1826 | 10 |
| LIP062_1827 | 100 |
| LIP062_1828 | 9 |
| LIP062_1829 | 10 |
| LIP062_1830 | 40 |
| LIP062_1831 | 200 |
| LIP062_1832 | 120 |
| LIP062_1833 | 140 |
| LIP062_1834 | 250 |
| LIP062_1835 | 40 |
| LIP062_1836 | 80 |
| LIP062_1837 | 67 |
| LIP062_1838 | 100 |
| LIP062_1839 | 50 |
| LIP062_1840 | 50 |
| LIP062_1841 | 90 |
| LIP062_1842 | 20 |
| LIP062_1843 | 40 |
| LIP062_1844 | 110 |
| LIP062_1845 | 65 |
| LIP062_1846 | 110 |
| LIP062_1847 | 90 |
| LIP062_1848 | 200 |
| LIP062_1849 | 40 |
| LIP062_1850 | 40 |
| LIP062_1851 | 90 |
| LIP062_1852 | 80 |
| LIP062_1853 | 200 |
| LIP062_1854 | 80 |
| LIP062_1855 | 20 |
| LIP062_1856 | 10 |
| LIP062_1857 | 50 |
| LIP062_1858 | 10 |
| LIP062_1859 | 90 |
| LIP062_1860 | 10 |
| LIP062_1861 | 45 |
| LIP062_1862 | 65 |
| LIP062_1863 | 100 |
| LIP062_1864 | 70 |
| LIP062_1865 | 70 |
| LIP062_1866 | 160 |
| LIP062_1867 | 200 |
| LIP062_1868 | 80 |
| LIP062_1869 | 100 |
| LIP062_1870 | 75 |
| LIP062_1871 | 85 |
| LIP062_1872 | 100 |
| LIP062_1873 | 65 |
| LIP062_1874 | 1 |
| LIP062_1875 | 30 |
| LIP062_1876 | 60 |
| LIP062_1877 | 130 |
| LIP062_1878 | 100 |
| LIP062_1879 | 150 |
| LIP062_1880 | 200 |
| LIP062_1881 | 150 |
| LIP062_1882 | 360 |
| LIP062_1883 | 6 |
| LIP062_1884 | 10 |
| LIP062_1885 | 41 |
| LIP062_1886 | 360 |
| LIP062_1887 | 40 |
| LIP062_1888 | 20 |
| LIP062_1889 | 26 |
| LIP062_1890 | 20 |
| LIP062_1891 | 14 |
| LIP062_1892 | 50 |
| LIP062_1893 | 30 |
| LIP062_1894 | n.d. |
| LIP062_1895 | n.d. |
| LIP062_1896 | n.d. |
| LIP062_1897 | n.d. |
| LIP062_1898 | n.d. |
| LIP062_1899 | n.d. |
| LIP062_1900 | n.d. |
| LIP062_1901 | n.d. |
| LIP062_1902 | n.d. |
| LIP062_1903 | n.d. |
| LIP062_1904 | 100 |
| LIP062_1905 | 100 |
| LIP062_1906 | 100 |
| LIP062_1907 | 100 |
| LIP062_1908 | 100 |
| LIP062_1909 | 100 |

Recovery

After filtering through cheese-cloth, the cell-free supernatants were ultrafiltered using a lab-scale tangential flow filtration (TFF) system with a molecular weight cut-off of 5 kD (SpectrumLabs). Samples were first concentrated 10-20× and then buffer-exchanged 5× into 50 mM HEPES pH 7.5. The resultant retentate was centrifuged at 27000×g for 1 hour, and then sterile filtered through 0.2 μm filters to remove any production organisms or particulate matter. Total protein content of the final samples was determined using the Braford assay. Lipases were lyophilized to form powder.

Example 3

Lipase Activity

The activity of the variant lipase enzymes was determined using natural substrates in solution. Natural lipid substrates were prepared at 5 mM final concentration in 0.25% sodium deoxycholate by sonication. Substrate (15 μL) was mixed with 30 uL fluorescein (0.25 μg/mL in 10 mM CaCl2) and 10 μL recovered lipase (~1-2 μg/mL) pre-diluted in 5 mM Hepes pH 7.5. Products of lipid hydrolysis were monitored by the drop in fluorescence due to pH change (485 nm/525 nm for excitation/emission), recorded kinetically every 30 seconds for 10 min at 26° C. Activity on a log scale was proportional with the fluorescence change per min. The results are shown below in Table 3, and the data is expressed as percentage of parent (LIP062) fluorescence change at same protein concentration. The activity of the variant lipase enzymes was not determined "n.d." for some of the variant lipase enzymes on some of the substrates; however, enough material was created as described in Example 2, and sent for amino acid sequence identification as described above in Example 1, Table 1.

TABLE 3

| Lipase | 1-Olein | Galactolipids | PC | C8-PNP | TAGs |
| --- | --- | --- | --- | --- | --- |
| LIP062 | 100 | 100 | 100 | 100 | 100 |
| LIP089 | 50 | 80 | 95 | n.d. | 45 |
| LIP090 | 85 | 60 | 70 | n.d. | 55 |
| LIP094 | 70 | 80 | 15 | 67 | 75 |
| LIP095 | 85 | 95 | 10 | 67 | 110 |
| LIP096 | 75 | 80 | 25 | 100 | 65 |
| LIP062_391 | 65 | 90 | 110 | 100 | 110 |
| LIP101 | 50 | 50 | 10 | 61 | 110 |
| LIP102 | 80 | 95 | 60 | 90 | 110 |
| LIP099 | 70 | 80 | 75 | 150 | 100 |
| LIP100 | 70 | 90 | 100 | 100 | 95 |
| LIP062_449 | 50 | 70 | 65 | 120 | 50 |
| LIP062_450 | 35 | 60 | 55 | 120 | 40 |
| LIP108 | 106 | 125 | 114 | 80 | 100 |
| LIP109 | 115 | 171 | 140 | 130 | 120 |
| LIP110 | 110 | 150 | 140 | 150 | 110 |
| LIP111 | 100 | 145 | 90 | 180 | 110 |
| LIP113 | 70 | 125 | 100 | 161 | 70 |
| LIP114 | 50 | 110 | 90 | 95 | 80 |
| LIP115 | 50 | 100 | 100 | 139 | 200 |
| LIP116 | 50 | 100 | 60 | 102 | 60 |
| LIP117 | 60 | 130 | 90 | 112 | 70 |
| LIP118 | 50 | 125 | 100 | 44 | 200 |
| LIP119 | 75 | 130 | 100 | 114 | 50 |
| LIP120 | 70 | 115 | 85 | 31 | 50 |
| LIP123 | 87 | 103 | 89 | 62 | 117 |
| LIP124 | 88 | 118 | 147 | 67 | 80 |
| LIP126 | 84 | 79 | 111 | 40 | 88 |
| LIP134 | 93 | 89 | 127 | n.d. | 78 |
| LIP135 | 85 | 76 | 116 | n.d. | 60 |
| LIP130 | 66 | 72 | 89 | 78 | 45 |
| LIP131 | 74 | 86 | 140 | 180 | 52 |
| LIP146 | 60 | 136 | 94 | n.d. | 74 |
| LIP147 | 69 | 186 | 142 | n.d. | 124 |
| LIP148 | 78 | 164 | 100 | n.d. | 131 |
| LIP149 | 57 | 128 | 44 | n.d. | 87 |
| LIP142 | 64 | 159 | 52 | n.d. | 70 |
| LIP143 | 81 | 214 | 86 | n.d. | 84 |
| LIP144 | 46 | 112 | 41 | n.d. | 66 |
| LIP145 | 76 | 164 | 85 | n.d. | 79 |
| LIP062_1664 | n.d. | n.d. | n.d. | n.d. | n.d. |
| LIP062_1665 | n.d. | n.d. | n.d. | n.d. | n.d. |
| LIP160 | 51 | 104 | 25 | n.d. | 102 |
| LIP062_1667 | n.d. | n.d. | n.d. | n.d. | n.d. |
| LIP062_1668 | n.d. | n.d. | n.d. | n.d. | n.d. |
| LIP062_1669 | n.d. | n.d. | n.d. | n.d. | n.d. |
| LIP062_1670 | n.d. | n.d. | n.d. | n.d. | n.d. |
| LIP161 | 51 | 129 | 5 | n.d. | 86 |
| LIP154 | 54 | 122 | 5 | n.d. | 100 |
| LIP162 | 60 | 131 | 10 | n.d. | 101 |
| LIP062_1674 | n.d. | n.d. | n.d. | n.d. | n.d. |
| LIP163 | 51 | 106 | 10 | n.d. | 79 |
| LIP062_1676 | n.d. | n.d. | n.d. | n.d. | n.d. |
| LIP062_1677 | n.d. | n.d. | n.d. | n.d. | n.d. |
| LIP062_1678 | n.d. | n.d. | n.d. | n.d. | n.d. |
| LIP165 | 43 | 105 | 6 | n.d. | 39 |
| LIP062_1680 | n.d. | n.d. | n.d. | n.d. | n.d. |
| LIP062_1681 | n.d. | n.d. | n.d. | n.d. | n.d. |
| LIP150 | 69 | 131 | 75 | n.d. | 80 |
| LIP062_1683 | n.d. | n.d. | n.d. | n.d. | n.d. |
| LIP062_1684 | n.d. | n.d. | n.d. | n.d. | n.d. |
| LIP062_1685 | n.d. | n.d. | n.d. | n.d. | n.d. |
| LIP062_1686 | n.d. | n.d. | n.d. | n.d. | n.d. |
| LIP155 | 53 | 94 | 9 | n.d. | 69 |
| LIP151 | 49 | 90 | 40 | n.d. | 70 |
| LIP156 | 44 | 111 | 22 | n.d. | 67 |
| LIP153 | 76 | 119 | 118 | n.d. | 82 |
| LIP062_1691 | n.d. | n.d. | n.d. | n.d. | n.d. |
| LIP062_1692 | n.d. | n.d. | n.d. | n.d. | n.d. |
| LIP159 | 50 | 121 | 9 | n.d. | 82 |
| LIP062_1694 | n.d. | n.d. | n.d. | n.d. | n.d. |
| LIP062_1695 | n.d. | n.d. | n.d. | n.d. | n.d. |
| LIP062_1696 | n.d. | n.d. | n.d. | n.d. | n.d. |
| LIP157 | 49 | 103 | 31 | n.d. | 109 |
| LIP158 | 81 | 180 | 61 | n.d. | 117 |
| LIP164 | 56 | 120 | 10 | n.d. | 68 |
| LIP062_1700 | n.d. | n.d. | n.d. | n.d. | n.d. |
| LIP062_1701 | n.d. | n.d. | n.d. | n.d. | n.d. |
| LIP152 | 57 | 116 | 24 | n.d. | 85 |
| LIP062_1703 | n.d. | n.d. | n.d. | n.d. | n.d. |
| LIP062_1704 | n.d. | n.d. | n.d. | n.d. | n.d. |
| LIP062_1766 | 29 | 59 | 0 | n.d. | 41 |
| LIP062_1767 | 39 | 75 | 8 | n.d. | 38 |
| LIP062_1768 | 27 | 54 | 0 | n.d. | 30 |
| LIP166 | 34 | 72 | 2 | n.d. | 47 |
| LIP062_1770 | 29 | 42 | 10 | n.d. | 37 |
| LIP167 | 59 | 118 | 8 | n.d. | 57 |
| LIP168 | 44 | 99 | 0 | n.d. | 59 |
| LIP062_1773 | 42 | 87 | 12 | n.d. | 33 |
| LIP062_1774 | 22 | 26 | 8 | n.d. | 33 |
| LIP062_1775 | 35 | 61 | 7 | n.d. | 46 |
| LIP062_1776 | 30 | 41 | 27 | n.d. | 53 |
| LIP169 | 59 | 118 | 3 | n.d. | 54 |
| LIP062_1778 | 41 | 73 | 10 | n.d. | 30 |
| LIP062_1779 | 20 | 55 | 4 | n.d. | 18 |
| LIP062_1780 | 47 | 86 | 19 | n.d. | 37 |
| LIP062_1781 | 39 | 59 | 5 | n.d. | 21 |
| LIP062_1782 | 24 | 52 | 1 | n.d. | 21 |
| LIP062_1788 | 51 | 105 | 17 | n.d. | n.d. |
| LIP170 | 75 | 160 | 20 | n.d. | 100 |
| LIP062_1790 | 95 | 123 | 128 | n.d. | n.d. |
| LIP171 | 65 | 138 | 7 | n.d. | 81 |
| LIP062_1792 | 87 | 117 | 17 | n.d. | n.d. |
| LIP062_1793 | 94 | 127 | 91 | n.d. | n.d. |
| LIP181 | 65 | 139 | 16 | n.d. | 104 |
| LIP062_1795 | 59 | 103 | 8 | n.d. | n.d. |
| LIP062_1796 | 78 | 120 | 40 | n.d. | n.d. |
| LIP062_1797 | 51 | 80 | 17 | n.d. | n.d. |
| LIP062_1798 | 47 | 72 | 0 | n.d. | n.d. |
| LIP062_1799 | 72 | 100 | 13 | n.d. | n.d. |
| LIP172 | 44 | 85 | 5 | n.d. | 69 |
| LIP062_1801 | 105 | 150 | 276 | n.d. | n.d. |
| LIP173 | 89 | 153 | 138 | n.d. | 98 |
| LIP062_1803 | 83 | 127 | 15 | n.d. | n.d. |
| LIP062_1804 | 87 | 115 | 16 | n.d. | n.d. |
| LIP062_1805 | 67 | 100 | 87 | n.d. | n.d. |
| LIP174 | 82 | 153 | 73 | n.d. | 94 |
| LIP062_1807 | 76 | 106 | 10 | n.d. | n.d. |
| LIP175 | 90 | 179 | 137 | n.d. | 106 |
| LIP178 | 60 | 109 | 18 | n.d. | 92 |

TABLE 3-continued

| Lipase | 1-Olein | Galactolipids | PC | C8-PNP | TAGs |
|---|---|---|---|---|---|
| LIP062_1810 | 59 | 90 | 10 | n.d. | n.d. |
| LIP176 | 86 | 169 | 12 | n.d. | 100 |
| LIP062_1812 | 78 | 105 | 43 | n.d. | n.d. |
| LIP177 | 106 | 185 | 168 | n.d. | 101 |
| LIP062_1814 | 66 | 91 | 67 | n.d. | n.d. |
| LIP179 | 87 | 148 | 40 | n.d. | 113 |
| LIP062_1816 | 110 | 141 | 19 | n.d. | n.d. |
| LIP062_1817 | 48 | 67 | 4 | n.d. | n.d. |
| LIP062_1818 | 83 | 119 | 17 | n.d. | n.d. |
| LIP180 | 68 | 99 | 7 | n.d. | 100 |
| LIP062_1820 | 87 | 125 | 37 | n.d. | n.d. |
| LIP182 | 63 | 132 | 5 | n.d. | 63 |
| LIP062_1822 | 51 | 75 | 3 | n.d. | n.d. |
| LIP062_1823 | 84 | 108 | 109 | n.d. | n.d. |
| LIP062_1824 | 83 | 113 | 144 | n.d. | n.d. |
| LIP062_1825 | 88 | 133 | 24 | n.d. | n.d. |
| LIP062_1826 | 15 | 25 | 25 | n.d. | 25 |
| LIP062_1827 | 1 | 60 | 0 | 1 | 0 |
| LIP062_1828 | 35 | 50 | 40 | 70 | 24 |
| LIP062_1829 | 40 | 50 | 3 | 70 | 4 |
| LIP062_1830 | 70 | 80 | 90 | 135 | 100 |
| LIP062_1831 | 130 | 100 | 100 | 50 | 80 |
| LIP062_1832 | 100 | 90 | 80 | 160 | 100 |
| LIP062_1833 | 120 | 110 | 90 | 130 | 120 |
| LIP062_1834 | 200 | 90 | 60 | 150 | 80 |
| LIP062_1835 | 90 | 70 | 80 | 100 | 80 |
| LIP062_1836 | 110 | 60 | 55 | 90 | 20 |
| LIP062_1837 | 90 | 50 | 40 | 160 | 90 |
| LIP062_1838 | 170 | 60 | 40 | 160 | 70 |
| LIP062_1839 | 120 | 65 | 50 | 3 | 0 |
| LIP062_1840 | 86 | 60 | 60 | 240 | 120 |
| LIP062_1841 | 140 | 80 | 60 | 20 | 0 |
| LIP062_1842 | 110 | 70 | 70 | 200 | 100 |
| LIP062_1843 | 55 | 40 | 25 | 260 | 90 |
| LIP062_1844 | 130 | 100 | 70 | 30 | 0 |
| LIP062_1845 | 180 | 80 | 24 | 35 | 0 |
| LIP062_1846 | 140 | 100 | 80 | 55 | 20 |
| LIP062_1847 | 150 | 80 | 20 | 20 | 15 |
| LIP062_1848 | 100 | 40 | 70 | 15 | 0 |
| LIP062_1849 | 90 | 55 | 60 | 30 | 120 |
| LIP062_1850 | 90 | 15 | 10 | 30 | 0 |
| LIP062_1851 | 110 | 50 | 0 | 20 | 0 |
| LIP062_1852 | 130 | 80 | 80 | 20 | 40 |
| LIP062_1853 | 100 | 70 | 45 | 10 | 0 |
| LIP062_1854 | 150 | 90 | 30 | 20 | 5 |
| LIP062_1855 | 0 | 0 | 0 | 0 | 0 |
| LIP062_1856 | 0 | 0 | 0 | 0 | 0 |
| LIP062_1857 | 5 | 5 | 5 | 5 | 5 |
| LIP062_1858 | n.d. | n.d. | n.d. | n.d. | n.d. |
| LIP062_1859 | 45 | 50 | 50 | 60 | 35 |
| LIP062_1860 | n.d. | n.d. | n.d. | n.d. | n.d. |
| LIP062_1861 | 21 | 2 | 1 | 26 | 18 |
| LIP062_1862 | 76 | 70 | 80 | 235 | 100 |
| LIP062_1863 | 76 | 76 | 46 | 100 | 67 |
| LIP062_1864 | 77 | 87 | 78 | 127 | 68 |
| LIP062_1865 | 35 | 22 | 21 | 70 | 34 |
| LIP062_1866 | 76 | 81 | 60 | 53 | 75 |
| LIP062_1867 | 46 | 47 | 12 | 148 | 47 |
| LIP062_1868 | 111 | 159 | 121 | 76 | 88 |
| LIP062_1869 | 107 | 154 | 126 | 74 | 87 |
| LIP062_1870 | 98 | 20 | 22 | 61 | 8 |
| LIP062_1871 | 144 | 112 | 43 | 88 | 86 |
| LIP062_1872 | 103 | 122 | 82 | 89 | 104 |
| LIP062_1873 | 80 | 12 | 10 | 138 | 78 |
| LIP062_1874 | 3 | 0 | 15 | 0 | 13 |
| LIP062_1875 | 68 | 55 | 89 | 299 | 85 |
| LIP062_1876 | 75 | 70 | 100 | 125 | 125 |
| LIP062_1877 | 70 | 70 | 95 | 70 | 110 |
| LIP062_1878 | n.d. | n.d. | n.d. | n.d. | n.d. |
| LIP062_1879 | n.d. | n.d. | n.d. | n.d. | n.d. |
| LIP062_1880 | n.d. | n.d. | n.d. | n.d. | n.d. |
| LIP062_1881 | n.d. | n.d. | n.d. | n.d. | n.d. |
| LIP062_1882 | 109 | 186 | 157 | 69 | 58 |
| LIP062_1883 | 47 | 37 | 57 | 73 | 71 |
| LIP062_1884 | 64 | 52 | 51 | 117 | 16 |
| LIP062_1885 | 53 | 79 | 65 | 201 | 92 |
| LIP062_1886 | 93 | 70 | 88 | 197 | 95 |
| LIP062_1887 | 60 | 51 | 58 | 47 | 81 |
| LIP062_1888 | 74 | 120 | 109 | 50 | 38 |
| LIP062_1889 | 59 | 88 | 73 | 73 | 57 |
| LIP062_1890 | 64 | 68 | 66 | 52 | 52 |
| LIP062_1891 | 57 | 54 | 59 | 135 | 44 |
| LIP062_1892 | 63 | 77 | 57 | 28 | 39 |
| LIP062_1893 | 41 | 37 | 16 | 12 | 22 |
| LIP062_1894 | 97 | 145 | 31 | n.d. | 142 |
| LIP062_1895 | 54 | 61 | 55 | n.d. | 67 |
| LIP062_1896 | 90 | 144 | 104 | n.d. | 114 |
| LIP062_1897 | 45 | 55 | 34 | n.d. | 56 |
| LIP062_1898 | 37 | 23 | 0 | n.d. | 76 |
| LIP062_1899 | 36 | 39 | 2 | n.d. | 70 |
| LIP062_1900 | 63 | 79 | 46 | n.d. | 105 |
| LIP062_1901 | 54 | 58 | 48 | n.d. | 78 |
| LIP062_1902 | 40 | 48 | 22 | n.d. | 131 |
| LIP062_1903 | 29 | 35 | 5 | n.d. | 149 |
| LIP062_1904 | 62 | 112 | 77 | n.d. | 42 |
| LIP062_1905 | 34 | 63 | 18 | n.d. | 37 |
| LIP062_1906 | 18 | 11 | 3 | n.d. | 19 |
| LIP062_1907 | 26 | 19 | 3 | n.d. | 25 |
| LIP062_1908 | 32 | 46 | 8 | n.d. | 25 |
| LIP062_1909 | 47 | 73 | 19 | n.d. | 31 |

Example 4

Lypolytic Enzyme Activity in Dough Assessed by HPLC

Simplified doughs were treated with several concentrations of variant lipase enzymes to determine their relative specific activity on flour lipids. Dough was prepared from 1 part flour and 2 parts water containing 34 mg/ml sodium chloride and enzymes at six concentrations: 0.02, 0.04, 0.2, 0.4, 2.0, 4.0 µg enzyme/500 µl dough. Doughs were mixed for 5 minutes at 3000 rpm then incubated in a humidity controlled chamber at 30° C. for a total of 60 minutes. For lipid analysis, 500 ul-butanol was added to each sample and the dough was homogenized by vortexing at 3000 rpm for 10 min. The solids were then separated by centrifugation at 4000×g for 5 minutes at room temperature. The organic phase was removed and directly injected for lipid analysis. Lipids were separated by HPLC (Agilent 1100 series) with a silica gel column (Chromolith Performance Si 100-4.6 mm, Merck) and analyzed by ELSD (Agilent 1260 Infinity). The chromatographic method for lipid separation was derived from Gerits, et. al. "Single run HPLC separation coupled to evaporative light scattering detection unravels wheat flour endogenous lipid redistribution during bread dough making" LWT-Food Science and Technology, 53 (2013) 426-433. The six enzyme doses and a negative control were used to determine if individual lipid classes (Table 4) increased, decreased or showed no change because of the enzyme treatment.

TABLE 4

Lipid Classes

| Abbreviation | Lipase Natural Substrates and Products |
|---|---|
| TAG | Triacyl glycerol |
| MGDG | Monogalactosyl diglyceride |
| DGDG | Digalactosyl diglyceride |
| NAPE | N-acylphosphatidyl ethanolamine |
| PC | Phosphatidyl choline |
| MAG | Monoacyl glycerol |
| DAG | Diacyl glycerol |
| FFA | Free fatty acid |

TABLE 4-continued

| Lipid Classes | |
|---|---|
| Abbreviation | Lipase Natural Substrates and Products |
| MGMG | Monogalactosyl monoglyceride |
| DGMG | Digalactosyl monoglyceride |

Table 5 shows the results of the changes in lipid class measurements relative to the parent enzyme. The Enzyme column of Table 5 lists the parent lipase enzymes (LIP062); and 70 different variant lipase enzymes, wherein the variant lipase enzymes have at least one amino acid modification when compared to the parent enzyme. In Table 5 the lipase variant activity on the substrates TAG, MGDG, DGDG, and NAPE is listed as a % relative to the parent lipase enzyme activity (LIP062). Table 5 also shows the accumulation of products (FFA, MAG, MGMG, and DGMG) for the variant lipase enzymes listed as a % relative to the parent lipase enzyme (LIP062).

TABLE 5

Analysis of Enzyme Activity in dough by HPLC

| Enzyme | TAG | FFA | MAG | MGDG | MGMG | DGDG | NAPE | DGMG |
|---|---|---|---|---|---|---|---|---|
| LIP062 | 100% | 100% | 100% | 100% | 100% | 100% | 100% | 100% |
| LIP061 | 110% | 154% | 88% | 84% | 11% | 128% | 140% | 537% |
| LIP088 | 69% | 81% | 72% | 56% | 6% | 37% | 82% | 208% |
| LIP089 | 19% | 47% | 24% | 74% | 27% | 50% | 44% | 13% |
| LIP090 | 51% | 109% | 47% | 126% | 102% | 118% | 93% | 115% |
| LIP094 | 20% | 34% | 24% | 48% | 20% | 27% | 27% | 46% |
| LIP095 | 39% | 78% | 67% | 111% | 66% | 83% | 94% | 89% |
| LIP096 | 10% | 78% | 44% | 17% | 82% | 28% | 28% | 122% |
| LIP099 | 104% | 127% | 96% | 132% | 120% | 108% | 103% | 96% |
| LIP100 | 134% | 190% | 111% | 283% | 227% | 201% | 161% | 371% |
| LIP101 | 4% | 31% | 2% | 80% | 50% | 44% | 31% | 20% |
| LIP102 | 69% | 112% | 62% | 105% | 76% | 89% | 100% | 86% |
| LIP108 | 69% | 100% | 44% | 154% | 138% | 201% | 177% | 301% |
| LIP109 | 68% | 210% | 79% | 179% | 147% | 325% | 166% | 137% |
| LIP110 | 116% | 161% | 79% | 196% | 103% | 307% | 214% | 188% |
| LIP111 | 117% | 135% | 107% | 120% | 113% | 201% | 87% | 335% |
| LIP113 | 95% | 227% | 65% | 276% | 364% | 361% | 177% | 798% |
| LIP114 | 129% | 265% | 64% | 202% | 375% | 376% | 194% | 1090% |
| LIP115 | 52% | 181% | 39% | 192% | 279% | 308% | 158% | 798% |
| LIP116 | 71% | 264% | 37% | 276% | 409% | 372% | 189% | 1130% |
| LIP117 | 97% | 191% | 24% | 278% | 194% | 460% | 237% | 647% |
| LIP118 | 70% | 283% | 45% | 185% | 360% | 370% | 177% | 924% |
| LIP119 | 15% | 82% | 8% | 138% | 103% | 224% | 75% | 964% |
| LIP120 | 18% | 104% | 6% | 362% | 510% | 267% | 145% | 298% |
| LIP122 | 2% | 127% | −8% | 88% | 7% | 290% | 15% | 1413% |
| LIP123 | 52% | 141% | 24% | 177% | 282% | 246% | 113% | 540% |
| LIP124 | 37% | 134% | 19% | 201% | 282% | 274% | 128% | 681% |
| LIP126 | 77% | 69% | 69% | 94% | 52% | 66% | 78% | 44% |
| LIP130 | 104% | 174% | 86% | 167% | 235% | 258% | 117% | 563% |
| LIP131 | 136% | 211% | 140% | 171% | 266% | 249% | 142% | 673% |
| LIP134 | 57% | 72% | 38% | 108% | 91% | 86% | 74% | 108% |
| LIP135 | 110% | 97% | 70% | 96% | 111% | 102% | 89% | 141% |
| LIP142 | 35% | 177% | 7% | 276% | 356% | 355% | 162% | 922% |
| LIP143 | 27% | 180% | 42% | 238% | 315% | 328% | 167% | 1327% |
| LIP144 | 15% | 155% | 15% | 141% | 140% | 251% | 140% | 628% |
| LIP145 | 19% | 142% | 33% | 238% | 205% | 282% | 125% | 804% |
| LIP146 | 35% | 119% | 41% | 154% | 145% | 226% | 121% | 688% |
| LIP147 | 74% | 205% | 80% | 238% | 209% | 321% | 172% | 1114% |
| LIP148 | 51% | 173% | 77% | 238% | 208% | 296% | 161% | 901% |
| LIP149 | 42% | 199% | 19% | 134% | 116% | 314% | 184% | 644% |
| LIP150 | 36% | 207% | 21% | 362% | 460% | 487% | 83% | 1915% |
| LIP151 | 70% | 217% | 50% | 212% | 123% | 320% | 154% | 479% |
| LIP152 | 121% | 237% | 82% | 216% | 171% | 418% | 213% | 688% |
| LIP153 | 88% | 144% | 55% | 179% | 138% | 296% | 154% | 485% |
| LIP155 | 94% | 73% | 23% | 135% | 88% | 231% | 61% | 261% |
| LIP156 | 6% | 102% | 7% | 33% | 44% | 90% | 28% | 320% |
| LIP158 | 143% | 260% | 313% | 238% | 319% | 323% | 152% | 915% |
| LIP159 | 48% | 105% | 25% | 238% | 205% | 264% | 76% | 788% |
| LIP160 | 79% | 137% | 86% | 238% | 205% | 283% | 146% | 967% |
| LIP161 | 14% | 112% | 23% | 238% | 182% | 282% | 26% | 840% |
| LIP162 | 33% | 115% | 36% | 238% | 227% | 286% | 56% | 1048% |
| LIP163 | 46% | 75% | 25% | 172% | 163% | 264% | 32% | 658% |
| LIP164 | 73% | 60% | 23% | 123% | 64% | 251% | 63% | 18% |
| LIP165 | 25% | 157% | 7% | 131% | 125% | 357% | 17% | 1378% |
| LIP166 | 98% | 43% | 17% | 151% | 70% | 281% | 133% | 242% |
| LIP167 | 43% | 287% | 19% | 213% | 204% | 535% | 183% | 2225% |
| LIP168 | 130% | 72% | 8% | 271% | 171% | 200% | 153% | 177% |
| LIP169 | 131% | 170% | 9% | 271% | 193% | 486% | 99% | 819% |
| LIP170 | 52% | 331% | 14% | 238% | 238% | 542% | 156% | 1956% |
| LIP171 | 59% | 109% | 11% | 129% | 104% | 312% | 34% | 540% |
| LIP172 | 2% | 180% | 0% | 141% | 119% | 346% | 20% | 375% |
| LIP173 | 63% | 261% | 59% | 72% | 109% | 309% | 167% | 1076% |

TABLE 5-continued

Analysis of Enzyme Activity in dough by HPLC

| Enzyme | TAG | FFA | MAG | MGDG | MGMG | DGDG | NAPE | DGMG |
|---|---|---|---|---|---|---|---|---|
| LIP174 | 77% | 209% | 79% | 52% | 100% | 311% | 60% | 772% |
| LIP175 | 102% | 483% | 14% | 249% | 386% | 536% | 247% | 3205% |
| LIP176 | 35% | 349% | 8% | 313% | 313% | 557% | 225% | 3026% |
| LIP177 | 144% | 359% | 68% | 223% | 217% | 488% | 237% | 880% |
| LIP178 | 25% | 219% | 8% | 234% | 234% | 526% | 92% | 1574% |
| LIP179 | 27% | 85% | 47% | 165% | 181% | 293% | 67% | 821% |
| LIP180 | 39% | 92% | 3% | 175% | 148% | 260% | 75% | 767% |
| LIP181 | 16% | 286% | 6% | 253% | 237% | 548% | 123% | 1844% |
| LIP182 | 5% | 131% | 1% | 283% | 191% | 401% | 93% | 1731% |

Example 5

Lipase Specific Activity at Various pH Values

The variant lipase enzymes were diluted at the appropriate concentration in 5 mM Hepes pH 7.5, then further diluted 16-fold into 0.4 mM PNP-octanoate prepared in broad range buffer of pH 6.5 to pH 12.0. The broad range buffer contained: 25 mM Phosphoric acid, 25 mM Citric Acid, 25 mM Boric Acid, 25 mM CAPS, and 50 mM NaCl. For pH 8.0, the buffer was supplemented with 10 mM Tris pH 8.0. Activity was measured at 26° C. by recording the absorbance at 405 nm every 40 seconds for 15 minutes. Activity was corrected for the background (no enzyme) and for the absorbance of PNP at each pH under identical conditions. The results are presented in Table 6, and the data is shown as micrograms PNP/min/mg enzyme.

22 g wheat starch, 120 ppm ascorbic acid, 5 ppm Nutrilife AM 100 (fungal alpha-amylase), 200 ppm Nutrilife CS 30 (fungal xylanase, cellulase, fungal alpha-amylase) and 1180 g water were mixed in a Kemper SP 15 spiral mixer for 5.5 minutes at speed 1 and 0.5 minutes at speed 2, to a final dough temperature of 28° C. After a resting for 12 minutes, the dough was scaled to a 1500 g piece, rounded and proofed for another 12 minutes. Afterwards, the dough was divided and rounded into 30 pieces of 50 g each by using an automatic dough divider and rounder. Then the dough pieces were proofed for 35 minutes (normal proof) and 45 minutes (extended proof) at 35° C. at relative humidity of 85%. After 12 minutes proofing time, a notch was pressed into the middle of the dough pieces. The proofed dough pieces were baked in a deck oven for 12 minutes at 240° C. with 15 seconds steam injection.

TABLE 6

Lipase Specific activity at various pH values (micrograms PNP/min/mg enzyme)

| pH | 6.5 | 7 | 7.5 | 8 | 8.5 | 9 | 9.5 | 10 | 10.5 | 11 | 11.5 | 12 |
|---|---|---|---|---|---|---|---|---|---|---|---|---|
| LIP062 | 801 | 1964 | 2972 | 4409 | 6258 | 7196 | 7621 | 7673 | 7378 | 6299 | 3027 | 67 |
| LIP108 | 1223 | 2699 | 3352 | 4889 | 6265 | 6952 | 7000 | 6970 | 6483 | 5300 | 2321 | 641 |
| LIP110 | 1547 | 3316 | 3977 | 5759 | 7572 | 7748 | 8168 | 7979 | 7605 | 6506 | 2829 | 0 |
| LIP117 | 1659 | 3930 | 4859 | 7023 | 8399 | 8633 | 8837 | 8873 | 8541 | 8320 | 2057 | 623 |
| LIP120 | 698 | 1565 | 2137 | 3495 | 5004 | 5837 | 5555 | 5517 | 5592 | 4415 | 1547 | 0 |
| LIP147 | 2148 | 4745 | 5294 | 7279 | 8469 | 8626 | 8903 | 8803 | 8174 | 7058 | 3290 | 0 |
| LIP148 | 1168 | 2322 | 2611 | 3350 | 4115 | 4306 | 4590 | 4309 | 4098 | 3182 | 1629 | 0 |
| LIP151 | 847 | 2442 | 3424 | 4695 | 6895 | 8135 | 7977 | 8073 | 7905 | 6615 | 1747 | 0 |
| LIP152 | 1397 | 4578 | 6733 | 9080 | 12819 | 14112 | 14469 | 14616 | 14249 | 13107 | 11190 | 3022 |
| LIP158 | 1558 | 5829 | 9207 | 13080 | 16994 | 17786 | 20804 | 20591 | 19884 | 17877 | 16228 | 3480 |
| LIP159 | 1597 | 6049 | 11246 | 16254 | 21623 | 23367 | 23500 | 24613 | 24755 | 23503 | 19089 | 3266 |
| LIP160 | 371 | 1989 | 3321 | 4587 | 7027 | 7793 | 6260 | 6777 | 6791 | 6746 | 5275 | 2778 |
| LIP161 | 658 | 2525 | 3417 | 2617 | 1354 | 1144 | 811 | 901 | 1006 | 1198 | 1563 | 2259 |
| LIP162 | 349 | 1789 | 3092 | 3998 | 6919 | 8499 | 7549 | 7997 | 8151 | 5403 | 2591 | 2320 |
| LIP167 | 865 | 4272 | 6674 | 9515 | 13479 | 14562 | 14354 | 14609 | 14067 | 14220 | 11058 | 2655 |
| LIP168 | 732 | 3227 | 5770 | 8165 | 12593 | 14811 | 14549 | 15625 | 15305 | 14363 | 12634 | 2594 |
| LIP170 | 744 | 2290 | 3953 | 5023 | 9480 | 11616 | 10958 | 11796 | 12121 | 10092 | 5869 | 0 |
| LIP171 | 721 | 2069 | 2412 | 1304 | 929 | 907 | 774 | 1072 | 1523 | 1649 | 1807 | 0 |
| LIP173 | 632 | 2700 | 4481 | 6758 | 10606 | 11937 | 12338 | 11999 | 10876 | 7959 | 0 | |
| LIP174 | 566 | 2145 | 3620 | 5323 | 9161 | 11201 | 9839 | 12847 | 13283 | 11964 | 9053 | 0 |
| LIP175 | 1339 | 4241 | 7361 | 10793 | 15578 | 16856 | 16903 | 18052 | 17557 | 13316 | 11183 | 0 |
| LIP176 | 1042 | 3504 | 5118 | 7951 | 12448 | 14183 | 13354 | 15648 | 15624 | 13333 | 7088 | 0 |
| LIP180 | 281 | 1365 | 2143 | 2618 | 4892 | 7405 | 6977 | 10671 | 12277 | 11056 | 4814 | 31 |
| LIP181 | 298 | 930 | 1229 | 1652 | 3163 | 4865 | 3739 | 5566 | 7607 | 6046 | 3805 | 31 |

Example 6

Baking Trails

The baking performance of the variant lipase enzymes was tested in a fast straight dough system, the Pistolet test. Ingredients using 2000 g of flour type 550 (Vogtmühlen Illertissen), 120 g compressed yeast, 40 g salt, 30 g glucose, The variant lipase enzymes, were tested up to six replicates per variant and the results are described in FIG. 1. These results are reported as an average of the replicates tested. Prior to the baking trials, each enzyme was tested for activity, which can vary between different enzymes, then each enzyme was tested to determine the optimum dosages for that enzyme, and finally the enzymes were added at the optimum dosage. For controls, 10-28 replicates have been used to calculate the average. The dosage for Panamore Golden 2.2 (PG2.2) (DSM) is based upon the manufactures recommendations at 0.68 mg lipase/kg flour. The dosage for DATEM, Lametop LT 552 (BASF), is 0.4% as recommended by the manufacturer. LIP062 is parent lipase enzyme for the lipase variants, used at an optimal dosage of 1 mg lipase/kg flour.

The effects of the variant lipase enzymes on the dough properties and on the final baked goods were compared to the parent lipase (LIP062), a negative control (no DATEM), and to a reference containing 0.4% (based on flour) DATEM (Lametop LT 552). The volume effect was determined by measurement of the length, width and height of 15 rolls in relation to the weight. The negative control is defined as 0%. Dough properties were evaluated by a skilled master baker and described in comparison to the negative control.

The invention claimed is:

1. A variant polypeptide comprising an amino acid sequence that has at least 80% sequence identity, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:1, wherein the variant polypeptide comprises an amino acid substitution at a residue corresponding to residue 83, 85, 264, 265, or 268 of SEQ ID NO: 1, and wherein the variant polypeptide has lipase activity.

2. The variant polypeptide of claim 1, wherein the amino acid substitution is selected from the group consisting of: S83D, S83H, S83I, S83N, S83R, S83T, S83Y, I85A, I85C, I85F, I85H, I85L, I85M, I85P, I85S, I85T, I85V, I85Y, T264A, T264D, T264G, T264I, T264L, T264N, T264S, D265A, D265G, D265K, D265L, D265N, D265S, D265T, T268A, T268G, T268K, T268L, T268N, and T268S, wherein the variant polypeptide has lipase activity.

3. The variant polypeptide of claim 1, wherein the variant polypeptide is encoded by a nucleic acid sequence that has at least 80% sequence identity to the nucleic acid sequence as set forth in SEQ ID NO:2, and the variant polypeptide has lipase activity.

4. A variant polypeptide comprising a hybrid of at least one variant polypeptide of claim 1 and a second polypeptide having lipase activity, wherein the hybrid has lipase activity.

5. A composition comprising the variant polypeptide of claim 1.

6. The composition of claim 5, further comprises a carrier, a stabilizer, a buffer, a preservative, or any combination thereof.

7. A composition comprising the variant polypeptide of claim 1 and at least a second enzyme.

8. The composition of claim 7, wherein the second enzyme is selected from the group consisting of: a second lipase, an amylase, a beta-amylase, a xylanase, a protease, a cellulase, a glucoamylase, an oxidoreductase, a phospholipase, and a cyclodextrin glucanotransferase.

9. A pre-mix for making dough or a baked product prepared from a dough, comprising the variant polypeptide of claim 1.

10. A variant polypeptide comprising an amino acid sequence that has at least 80% sequence identity, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:1, wherein the variant polypeptide has at least one amino acid substitution at a residue corresponding to residue 83, 85, 254, 255, 264, 265, or 268 of SEQ ID NO:1, and the at least one amino acid substitution is selected from the group consisting of: S83D, S83H, S83I, S83N, S83R, S83T, S83Y, I85A, I85C, I85F, I85H, I85L, I85M, I85P, I85S, I85T, I85V, I85Y, I254A, I254C, I254E, I254F, I254G, I254L, I254M, I254N, I254R, I254S, I254W, I254Y, I255A, I255L, T264A, T264D, T264G, T264I, T264L, T264N, T264S, D265A, D265G, D265K, D265L, D265N, D265S, D265T, T268A, T268G, T268K, T268L, T268N, T268S, and D308A, and wherein the variant polypeptide has lipase activity.

11. A method of preparing a dough or a baked product prepared from the dough, without the addition of an emulsifier, the method comprising adding the variant polypeptide of claim 1 to the dough and baking it.

12. The method of claim 11, wherein the emulsifier is selected from the group consisting of: calcium stearoyl lactylate (CSL), diacetyl tartaric acid esters of monoglycerides (DATEM), ethoxylated mono- and diglycerides (EMG), polysorbates (PS), sodium stearoyl lactylate (SSL), and succinylated monoglycerides (SMG).

\* \* \* \* \*

SEQUENCE LISTING

```
<160> NUMBER OF SEQ ID NOS: 2

<210> SEQ ID NO 1
<211> LENGTH: 317
<212> TYPE: PRT
<213> ORGANISM: Fusarium solani

<400> SEQUENCE: 1

Ala Ile Thr Ala Ser Gln Leu Asp Tyr Glu Asn Phe Lys Phe Tyr Ile
1               5                   10                  15

Gln His Gly Ala Ala Tyr Cys Asn Ser Glu Thr Ala Ser Gly Gln
            20                  25                  30

Lys Ile Thr Cys Ser Asp Asn Gly Cys Lys Gly Val Glu Ala Asn Asn
            35                  40                  45

Ala Ile Ile Val Ala Ser Phe Val Gly Lys Gly Thr Gly Ile Gly Gly
        50                  55                  60

Tyr Val Ser Thr Asp Asn Val Arg Lys Glu Ile Val Leu Ser Ile Arg
65                  70                  75                  80

Gly Ser Ser Asn Ile Arg Asn Trp Leu Thr Asn Val Asp Phe Gly Gln
                85                  90                  95

Ser Ser Cys Ser Tyr Val Arg Asp Cys Gly Val His Thr Gly Phe Arg
            100                 105                 110

Asn Ala Trp Asp Glu Ile Ala Gln Arg Ala Arg Asp Ala Val Ala Lys
            115                 120                 125

Ala Arg Thr Met Asn Pro Ser Tyr Lys Val Ile Ala Thr Gly His Ser
        130                 135                 140

Leu Gly Gly Ala Val Ala Thr Leu Gly Ala Ala Asp Leu Arg Ser Lys
145                 150                 155                 160

Gly Thr Ala Val Asp Ile Phe Thr Phe Gly Ala Pro Arg Val Gly Asn
                165                 170                 175

Ala Glu Leu Ser Ala Phe Ile Thr Ala Gln Ala Gly Gly Glu Phe Arg
            180                 185                 190

Val Thr His Gly Arg Asp Pro Val Pro Arg Leu Pro Pro Ile Val Phe
            195                 200                 205

Gly Tyr Arg His Thr Ser Pro Glu Tyr Trp Leu Ala Gly Gly Ala Ser
        210                 215                 220

Thr Lys Thr Asp Tyr Thr Val Asn Asp Ile Lys Val Cys Glu Gly Ala
225                 230                 235                 240

Ala Asn Leu Ala Cys Asn Gly Gly Thr Leu Gly Leu Asp Ile Ile Ala
                245                 250                 255

His Leu Arg Tyr Phe Gln Asp Thr Asp Ala Cys Thr Ala Gly Gly Ile
            260                 265                 270

Ser Trp Lys Arg Gly Asp Lys Ala Lys Arg Asp Glu Ile Pro Lys Arg
        275                 280                 285

Gln Glu Gly Met Thr Asp Glu Glu Leu Glu Gln Lys Leu Asn Asp Tyr
    290                 295                 300
```

```
Val Ala Met Asp Lys Glu Tyr Val Glu Ser Asn Lys Met
305                 310                 315

<210> SEQ ID NO 2
<211> LENGTH: 954
<212> TYPE: DNA
<213> ORGANISM: Fusarium solani

<400> SEQUENCE: 2
gccattactg cttctcaatt ggactacgaa aacttcaagt tttacatcca gcacggtgcc    60
gctgcttact gtaactccga aactgcctct ggtcaaaaga tcacttgttc cgacaacggt   120
tgcaaaggtg tcgaagctaa caacgctatt attgtcgcct ctttcgttgg aaaaggtact   180
ggtattggtg gttacgtttc tactgataac gttagaaagg agatcgtttt gtctattaga   240
ggttcttcca acattcgtaa ctggttgact aacgtcgact tcggacaatc ctcttgttct   300
tacgttagag attgtggagt tcacactggt ttcagaaatg cttgggacga gattgcccaa   360
agagctagag acgctgtcgc taaagctaga actatgaacc catcttacaa ggttatcgct   420
actggtcact cttttgggtgg tgctgttgcc actttgggtg ctgctgattt gagatccaag   480
ggtactgccg tcgatatctt tactttggt gccccaagag ttggtaacgc tgagttgtcc   540
gctttcatca ctgctcaggc tggtggtgag ttcagagtta ctcacggacg tgatccagtt   600
ccacgtttgc cacctatcgt cttcggttac agacacacct ctccagagta ctggttggct   660
ggtggtgctt ccaccaagac tgattatact gttaacgata tcaaggtttg tgaaggtgcc   720
gctaacttgg cctgtaatgg tggtactttg ggattggata tcattgctca tttgagatac   780
ttccaagaca ctgacgcctg tactgctggt ggtatctcct ggaagagagg tgacaaagct   840
aagagagatg agattccaaa aagacaagaa ggaatgactg atgaggagtt ggaacaaaaa   900
ctgaacgact atgtcgccat ggataaggag tacgttgagt ccaacaagat gtaa          954
```